United States Patent
Abbas et al.

(10) Patent No.: US 9,388,399 B2
(45) Date of Patent: Jul. 12, 2016

(54) **DEVELOPMENT OF STRAINS OF THE THERMOTOLERANT YEAST *HANSENULA POLYMORPHA* CAPABLE OF ALCOHOLIC FERMENTATION OF STARCH AND XYLAN BY EXPRESSION OF STARCH AND XYLAN DEGRADING ENZYMES**

(75) Inventors: Charles Abbas, Champaign, IL (US); Andriy Sibirny, Lviv (UA); Andriy Y. Voronovsky, Lviv (UA)

(73) Assignee: Archer Daniels Midland Company, Decatur, IL (US)

( * ) Notice: Subject to any disclaimer, the term of this patent is extended or adjusted under 35 U.S.C. 154(b) by 76 days.

(21) Appl. No.: 12/989,735

(22) PCT Filed: May 6, 2009

(86) PCT No.: PCT/US2009/042975
§ 371 (c)(1),
(2), (4) Date: Oct. 26, 2010

(87) PCT Pub. No.: WO2009/137574
PCT Pub. Date: Nov. 12, 2009

(65) Prior Publication Data
US 2011/0045562 A1    Feb. 24, 2011

Related U.S. Application Data

(60) Provisional application No. 61/050,685, filed on May 6, 2008.

(51) Int. Cl.
*C12N 9/34* (2006.01)
*C12N 9/28* (2006.01)
*C12P 7/06* (2006.01)
*C12N 9/30* (2006.01)
*C12N 9/26* (2006.01)

(52) U.S. Cl.
CPC ............ *C12N 9/2428* (2013.01); *C12N 9/242* (2013.01); *C12N 9/2414* (2013.01); *C12P 7/06* (2013.01); *C12Y 302/01001* (2013.01); *C12Y 302/01003* (2013.01); *C12Y 302/01008* (2013.01); *C12Y 302/01037* (2013.01); *C12Y 401/01001* (2013.01); *Y02E 50/17* (2013.01); *Y02P 20/52* (2015.11)

(58) Field of Classification Search
CPC ....... C12P 2203/00; C12P 7/06; C12N 15/81; C12N 15/65; C12Y 302/01001

USPC .................. 435/320.1, 254.11, 161, 202, 96
See application file for complete search history.

(56) References Cited

U.S. PATENT DOCUMENTS 5,100,794 A * 3/1992 Strasser ................ A21D 8/047
                                                              435/202
5,487,989 A * 1/1996 Fowler ................ C12N 9/0006
                                                              435/162

OTHER PUBLICATIONS

Reiser et al adv bioeng and biotech 1990 43 pp. 75-102.*
Kisselev L., Structure, 2002, vol. 10: 8-9.*
Whisstock et al., Quarterly Reviews of Biophysics 2003, vol. 36 (3): 307-340.*
Devos et al., Proteins: Structure, Function and Genetics, 2000, vol. 41: 98-107.*
Witkowski et al., Biochemistry 38:11643-11650, 1999.*
Reiser et al. ADv Biochem. Eng.1990, 43, pp. 75-102.*
Hartner et al. Microbial cell factories, 2006 pp. 1-21.*
Ryabova et al. FEMS Yeast Res. 2003, 4, pp. 157-164.*

* cited by examiner

*Primary Examiner* — Md. Younus Meah
(74) *Attorney, Agent, or Firm* — Corey Crafton

(57) ABSTRACT

Genes SWA2 and GAM1 from the yeast, *Schwanniomyces occidentalis*, encoding α-amylase and glucoamylase, respectively, were cloned and expressed in *H. polymorpha*. The expression was achieved by integration of the SWA2 and GAM1 genes into the chromosome of *H. polymorpha* under operably linked to a strong constitutive promoter of the *H. polymorpha*-glyceraldehyde-3-phosphate dehydrogenase gene (HpGAP. Resulting transformants acquired the ability to grow on a minimal medium containing soluble starch as a sole carbon source and can produce Ethanol at high-temperature fermentation from starch up to 10 g/L. A XYN2 gene encoding endoxylanase was obtained from the fungus *Trichoderma resee*, and a xlnD gene coding for β-xylosidase was obtained from the fungus *Aspergillus niger*. Co-expression of these genes was also achieved by integration into the *H. polymorpha* chromosome under control of the HpGAP promoter. The resulting transformants were capable of growth on a minimal medium supplemented with birchwood xylan as a sole carbon source. Successful expression of xylanolytic enzymes resulted in a recipient strain capable of fermentation of birchwood xylan to ethanol at 48° C. Further with co expression of the forgoing genes in a *H. polymorpha* strain that overexpresses a pyruvate decarboxylase gene further improved ethanol production.

7 Claims, 23 Drawing Sheets

Minimal medium + 2% starch

Minimal medium + 2% starch + 1% glucose

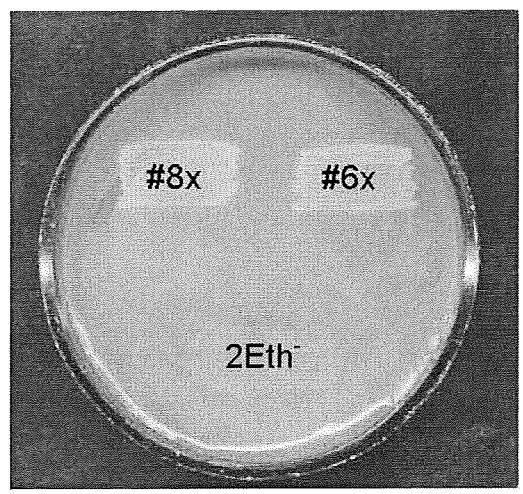
Minimal medium
+ 3% birchwood xylan
Fig. 17A
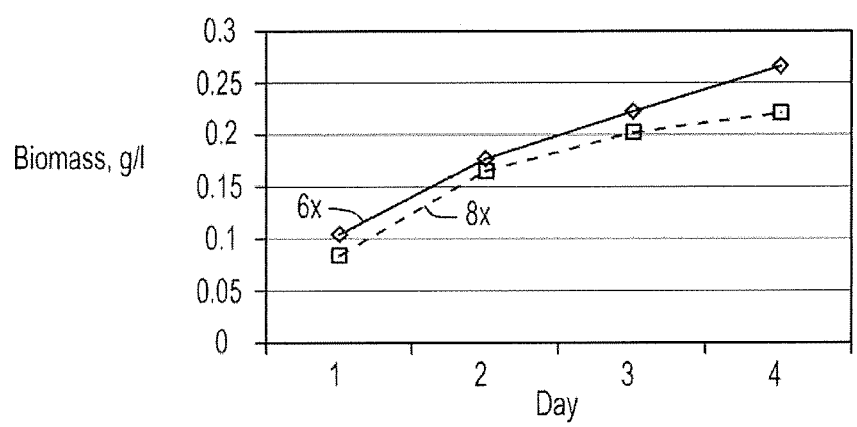
Fig. 17B1
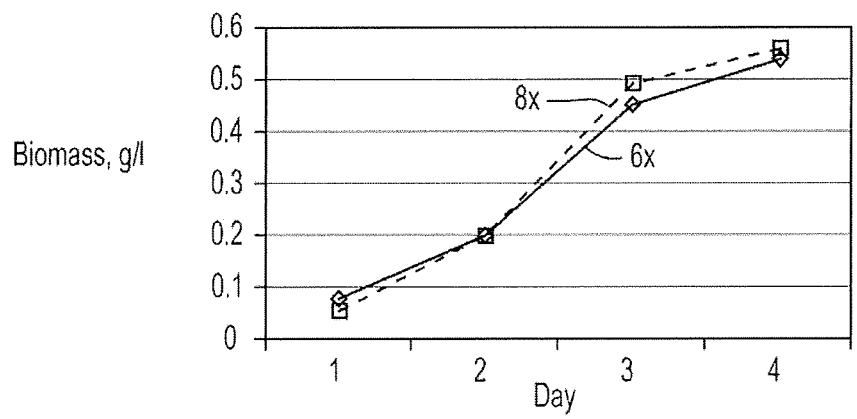
Fig. 17B2

Minimal medium+2%Glc+1mM PNPX

Visualization of the β-xylosidase secretion

Minimal medium+2%Glc+0.2% RBB-xylan

Visualization of the endoxylanase secretion

Figure 20A

```
GGATCCCAATTATCATTAATAATCACTCATGATCCCTGCGTCTAGAGGTTGGTCTAGACCACATCCGTGCACCAGAC
AAGACACGGCCCACGGAGGTAAAGGTGCCAACTCGCAAAGTGCAACAACCATGGCTCTCCAGCACGGTGCGTGGGGT
AAAGACAATCTCCGGGAACCGATCCCGAAACCGAGAAAGAGGGTTTTAAGCGTGTGTCCTTTGCGGAGGCGGTGTAG
CACTTCTTATTGTCCTTTGGGCCGCTCCGGCGGTTGAGCTTCCACAGAACATCCTTGCACGGACAAGCAGTCCCGGA
GACGCCATGTTGGGTGATACCCACTTCTGGCTGTACAGAGCTTTATATCACCTTACCTGGCGCTAGAGTAGACCCAA
TTCCCGACTCACACCACCCTCACATGCAGAACTAACCAATAAGGTAATTAATTAACACGATATAGCTCGTGGTGAAC
ACTGGCCCGGAGTAGTCATACGTGTAGGTTTTTGGCGTGATGAAAATCAGGTGGAGCACGACTTTTCGTAATGTTCG
GGAGGGAGTGCTGCAAACGGTATATAAGGACCAGTTTTTCTCGCAACATTATCAATTGCTCTTTAGTACAAAGATAA
TATAGAAACAAACATATGAGATTTTCAACTGAAGGATTTACAAGTAAAGTTGTTGCAGCAATTTTAGCATTCTCAAG
ATTGGTATCTGCTCAACCGATTATTTTTGACATGAGAGATGTTAGCTCGTCAGCTGATAAATGGAAAGACCAATCGA
TTTATCAAATCGTTACTGATAGGTTTGCCAGATCTGATGGCTCGACCACAGCTGACTGTTTAGTGAGTGATCGCAAG
TACTGTGGTGGATCTTATAAAGGGATTATCGACAAGTTGGATTATATTCAAGGTATGGGTTTCACTGCGATCTGGAT
CTCCCCAGTTGTTGAGCAAATTCCTGACAATACTGCTTATGGTTATGCTTACCATGGTTATTGGATGAAAAATATTG
ATGAATTGAACACTAATTTTGGTACCGCTGATGAATTGAAACAATTAGCTAGCGAATTGCATTCCAGAAGCATGTTA
TTGATGGTCGACGTTGTTTACAACCATTATGCTTGGAACGGAGATGGTTCAAGCGTAGATTATTCTAGTTTCACTCC
ATTCAATCAACAATCTTACTTCCACGATTATTGTTTGATTACAAATTATAATGATCAAACCAATGTTGAAGATTGTT
GGGAAGGTGATACTGAAGTCTCCCTTCCAGATTTAAGTACCGAGGATAATGAAGTTATAGGAGTATTTCAAACTTGG
GTGTCAGATTTTGTTCAAAACTATTCAATCGATGGTTTAAGAATTGATAGTGCAAAGCACGTAGATACCGCTTCATT
AACGAAGTTTGAGGACGCTTCTGGTGTTTATAACTTAGGTGAAGTTTATCAAGGAGATCCAACTTATACTTGTCCAT
ATCAGAATTATATGAAAGGAGTTACCAACTATCCATTATACTATCCAGTATATAGATTCTTCAGTGATACTTCGGCG
ACTTCCAGTGAGTTAACTTCAATGATCTCCACGTTACAGTCATCTTGTTCGGACGTCTCTTTGTTGGGAAACTTTAT
TGAAAACCATGACCAAGTTAGATTTCCATCAGTTACCTCAGACACATCCTTGATTAAGAATGACATGGCTTTTATAA
TTTTGGGTGATGGTATCCCAATTATTTATTATGGCCAAGAACAAGGTCTCAATGGTGGTTCCGATCCTGCCAATAGA
GAAGCTTTATGGTTAAGTGGATATAATACCGATTCAGAATACTACGAGCTAATCAGTAAACTAAATCAAATAAGAAA
TCAAGCTATTAAGAAGGATTCTGCCTATTCAACTTACAAATCCTCAGTTGTTTCTTCTTCAGACCACTATATAGCCA
CTAGGAAGGGTAGCGATGCTAATCAATTGATTTCCATTTTTAATAATTTAGGTTCAAACGGGTCACAGGATATTACT
GTCAGCAACACCGGCTATTCTAGTGGTGATAAAGTTATCGATATTATTTCTTGCAATTCCGTTTTAGCTGGTGACTC
CGGAAGCTTATCTGTATCAATTTCTGGTGGAATGCCACAAGTTTACGCTCCGTCCTCTGTTCTTTCGGGATCTGGCA
TCTGCAATCAATAGAGCTTGGAGACCTCAAGGACATACCGCTTTTGAGAAGCGTGTTTGAAAATACTTCTTTTCT
GGTTTATATCGTTTATGAAGTGATCAGATGAAAAGCTGAAATAGCGAGTATACGAAAATTTAATCAAATTAAATTA
AATATTTTCTTAGGCTATTAGTCACCTTCAAAATGCCGGCCGCTTCTAAGAACGTTGTCATGATCGACAACTACGAC
TCGTTTACCTGGAACCTGTACGAGTACCTGTGTCAGGAGGGAGCCAATGTCGAGCTTTTCAGGAACGATCAGATCAC
CATTCCGGAGATTCAGCAGCTCAAGCCGGACGTTGTGGTGATATCCCCTGGTCCTGGCCATCCAAGAACAGACTCGG
GAATATCTCGCGACGTGATCACCCATTTTAAAGGCAACATTGGATCC
```

Figure 20B

```
MRFSTEGFTSKVVAAILAFSRLVSAQPIIFDMRDVSSSADKWKDQSIYQIVTDRFARSDGSTTADCLVSDRKYCGGS
YKGIIDKLDYIQGMGFTAIWISPVVEQIPDNTAYGYAYHGYWMKNIDELNTNFGTADELKQLASELHSRSMLLMVDV
VYNHYAWNGDGSSVDYSSFTPFNQQSYFHDYCLITNYNDQTNVEDCWEGDTEVSLPDLSTEDNEVIGVFQTWVSDFV
QNYSIDGLRIDSAKHVDTASLTKFEDASGVYNLGEVYQGDPTYCPYQNYMKGVTNYPLYYPVYRFFSDTSATSSEL
TSMISTLQSSCSDVSLLGNFIENHDQVRFPSVTSDTSLIKNDMAFIILGDGIPIIYYGQEQGLNGGSDPANREALWL
SGYNTDSEYYELISKLNQIRNQAIKKDSAYSTYKSSVVSSSDHYIATRKGSDANQLISIFNNLGSNGSQDITVSNTG
YSSGDKVIDIISCNSVLAGDSGSLSVSISGGMPQVYAPSSVLSGSGICNQ
```

Figure 21A

GGATCCCAATTATCATTAATAATCACTCATGATCCCTGCGTCTAGAGGTTGGTCTAGACCACATCCGTGCACCAGACAAGACACGG
CCCACGGAGGTAAAGGTGCCAACTCGCAAAGTGCAACAACCATGGCTCTCCAGCACGGTGCGTGGGGTAAAGACAATCTCCGGGAA
CCGATCCCGAAACCGAGAAAGAGGGTTTTAAGCGTGTGTCCTTTGCGGAGGCGGTGTAGCACTTCTTATTGTCCTTTGGGCCGCTC
CGGCGGTTGAGCTTCCACAGAACATCCTTGCACGGACAAGCAGTCCCGGAGACGCCATGTTGGGTGATACCCACTTCTGGCTGTAC
AGAGCTTTATATCACCTTACCTGGCGCTAGAGTAGACCCAATTCCCGACTCACACCACCCTCACATGCAGAACTAACCAATAAGGT
AATTAATTAACACGATATAGCTCGTGGTGAACACTGGCCCGGAGTAGTCATACGTGTAGGTTTTTGGCGTGATGAAAATCAGGTGG
AGCACGACTTTTCGTAATGTTCGGGAGGGAGTGCTGCAAACGGTATATAAGGACCAGTTTTTCTCGCAACATTATCAATTGCTCTT
TAGTACAAAGATAATATAGAAACAAAAAGCTTATGATTTTTCTGAAGCTGATTAAAAGTATAGTAATTGGTTTGGGATTAGTTAGT
GCTATCCAAGCAGCCCCTGCCTCTTCGATTGGATCTAGTGCTTCAGCATCTAGTTCAAGTGAGAGTTCTCAGGCTACAATTCCCAA
TGATGTAACATTAGGTGTTAAACAAATTCCTAATATCTTTAATGACTCTGCTGTCGATGCTAATGCAGCTGCTAAAGGGTATGACT
TGGTAAATGTTACTAATACTCCAAGAGGATTAACCGGTATCTTAAAATTAAAAGAAGCTACCAATATTTATGGTTATGATTTTGAT
TATTTAAACTTAACTGTTGAATACCAAGCTGATACCAGATTAAACGTTCATATTGAACCAACTGATTTATCTGATGTATTTGTTTT
ACCAGAGCATTTAGTTGTTAAACCACTGGTGGAAGGTGATGCACAATCTTATAACTTCGACAATTCCGATTTGGTTTTCGAATACT
CTAATACTGACTTCTCCTTTGAAGTTATTAGATCATCTACTAAAGAAGTTTTATTTTCTACTAAAGGTAATCCATTGGTTTTTTCA
AATCAATTCATTCAATTCAATTCGTCATTGCCAAAGAACCATGTTATTACTGGTCTTGGTGAATCTATTCACGGTTTAGTTAACGA
ACCAGGTAGCGTTAAAACATTATTTGCTAATGATGTTGGTGATCCAATCGATGGTAATATTTATGGTGTCCATCCAGTTTATCTTG
ATCAAAGATATGACACTGAAACTACCCATGCTGTTTATTGGAGAACTTCTGCTATTCAAGAAGTATTAATCGGTGAGGAATCTATT
ACTTGGAGAGCTCTTTCAGGTGTTATTGATTTATACTTCTTTAGTGGTCCTACACCAAAAGATGCCATTCAACAGTATGTCAAAGA
GATTGGTTTACCAGCTTTCCAACCATACTGGTCGTTAGGTTACCATCAATGTAGATGGGGTTACGATACTATCGAAAAATTATCTG
AAGTTGTTGAAAACTTCAAGAAATTTAATATTCCATTAGAAACTATCTGGTCAGACATTGATTACATGGACTCTTATAAAGATTTC
ACTTATGATCCACACAGATTCCCACTAGATGAATATCGTAAATTCCTTGATGAGTTGCACAAAAATAATCAACACTATGTTCCTAT
TTTGGATGCTGCTATTTACGTTCCAAACCCAAACAATGCTACGGATAACGAATACCAACCTTTCCACTATGGTAATGAAACCGATG
TCTTCTTAAAGAATCCAGATGGTTCATTATATATTGGTGCTGTTTGGCAGGTTACACTGTTTTCCAGATTTCTTAGCAGAAAACAT
TCAGATATGGATAAAGTCATTAAAGATTGGTATGAATTAACTCCTTTTGATGGTATTTGGGCTGATATGAATGAAGTCTCATCATT
CTGTGTTGGTTCTTGTGGTACTGGTAAATACTTCGAAAACCCAGCATATCCTCCATTTACTGTTGGAAGTAAAGCTACCTCTTATC
CAGTTGGTTTCGATGTTTCTAACGCATCTGAATGGAAATCTATTCAAAGCTCAATTTCTGCTACTGCTAAGACTTCTTCAACTTCT
TCCGTATCGTCGTCTTCATCCACAATCGATTATATGAACACTTTAGCTCCAGGTAAAGGTAATATTAATTATCCACCATATGCTAT
TTACAACATGCAAGGTGACTCCGATCTTGCTACTCATGCAGTATCTCCAAATGCTACACATGCTGATGGTACAGTTGAATATGATA
TTCACAATCTTTATGGTTACTTGCAAGAAAATGCTACTTATCATGCATTATTGGAAGTTTTTCCTAACAAGAGACCATTCATGATT
TCCAGATCAACCTTTCCACGCGCTGGTAAATGGACCGGCCATTGGGGTGGTGACAACACTGCTGATTGGCTTATGCTTACTTCTC
TATCCCTCAAGCATTCTCAATGGGTATTGCTGGCCTTCCATTCTTTGGTGCCGATGTTTGTGGTTTCAATGGTAATTCTGATTCTG
AATTATGTTCAAGATGGATGCAATTAGGTTCTTTCTTCCCATTCTACAGAAACCACAACTATTTAGGTGCTATTGATCAGGAACCA
TATGTCTGGGAATCAGTTGCTGAAGCTACTAGAACTTCTATGGCCATTAGATACTTATTATTACCATATTACTACACTTTATTACA
TGAATCTCATACTACTGGTTTACCAATCTTAAGAGCTTTCTCGTGGCAATTCCCTAACGATCGTTCCTTAAGTGGTGTCGATAACC
AATTTTTTGTCGGTGATGGTTTAGTTGTTACTCCTGTCTTAGAACCTGGTGTTGATAAGGTTAAAGGTGTTTTCCCAGGAGCTGGT
AAAGAGGAAGTTTACTACGACTGGTACACCCAAAGAGAAGTTCACTTTAAAGACGGTAAGAATGAAACTTTAGATGCACCATTAGG
TCATATTCCATTACACATTAGAGGTGGTAACGTCTTGCCAACTCAAGAGCCAGGTTATACTGTTGCTGAGTCAAGACAAAATCCAT
TTGGTTTAATTGTCGCTTTAGATAACGATGGCAAAGCTCAAGGTAGCTTATACCTTGATGATGGTGAATCATTAGTAGTAGACTCT
TCATTGTTGGTTAGTTTCTCTGTTTCTGATAACACATTATCAGCATCTCCATCTGGTGACTATAAAGCTGATCAACCTTTAGCTAA
TGTTACCATCTTAGGGGTTGGCCATAAACCAAAATCAGTTAAATTTGAAAACGCTAATGTTGATTTCACCTACAAGAAATCAACCG
TTTTCGTTACTGGCTTAGATAAATACACCAAGGATGGTGCATTTTCTAAGGATTTCACCATTACTTGGTAA*TTTAACATCCACTT*
*AGTTCAATTCCATTCTTTTCTTTTTCCCGTGAAATTCTGAATTTGAAATTATTTGAATGATATCATTTTAGTTTTCTTCAGCTTAT*
*GCTATGTTTATTTCGATTTAAATGTTAAAAGTTTTTTATGTTTATGTTGTTTTATTGATGTAGTTGATAAAATATAGCAAATACA*
*TCGAAAAATTTGCGATGAAATTTTGCAGCTCATTAGAAATGTAGTCAATCATTAGTCACATTGGACCACTATATAACAAACAACAA*
*CTATTCCAAGAAAATATATGTAAGGATACTAGATCATAAATTCTTATTGACTTTGTTTTTTTTAACAATAGTTACATAAGGAATA*
*TTCGTTTACTACAAAACCATTGGTCTTGTAAAGAA*

Figure 21B

MIFLKLIKSIVIGLGLVSAIQAAPASSIGSSASASSSSESSQATIPNDVTLGVKQIPNIFNDSAVDANAAAKGYDLVNVTNTPRGL
TGILKLKEATNIYGYDFDYLNLTVEYQADTRLNVHIEPTDLSDVFVLPEHLVVKPLVEGDAQSYNFDNSDLVFEYSNTDFSFEVIR
SSTKEVLFSTKGNPLVFSNQFIQFNSSLPKNHVITGLGESIHGLVNEPGSVKTLFANDVGDPIDGNIYGVHPVYLDQRYDTETTHA
VYWRTSAIQEVLIGEESITWRALSGVIDLYFFSGPTPKDAIQQYVKEIGLPAFQPYWSLGYHQCRWGYDTIEKLSEVVENFKKFNI
PLETIWSDIDYMDSYKDFTYDPHRFPLDEYRKFLDELHKNNQHYVPILDAAIYVPNPNNATDNEYQPFHYGNETDVFLKNPDGSLY
IGAVWQVTLFSRFLSRKHSDMDKVIKDWYELTPFDGIWADMNEVSSFCVGSCGTGKYFENPAYPPFTVGSKATSYPVGFDVSNASE
WKSIQSSISATAKTSSTSSVSSSSSTIDYMNTLAPGKGNINYPPYAIYNMQGDSDLATHAVSPNATHADGTVEYDIHNLYGYLQEN
ATYHALLEVFPNKRPFMISRSTFPRAGKWTGHWGGDNTADWAYAYFSIPQAFSMGIAGLPFFGADVCGFNGNSDSELCSRWMQLGS
FFPFYRNHNYLGAIDQEPYVWESVAEATRTSMAIRYLLLPYYYTLLHESHTTGLPILRAFSWQFPNDRSLSGVDNQFFVGDGLVVT
PVLEPGVDKVKGVFPGAGKEEVYYDWYTQREVHFKDGKNETLDAPLGHIPLHIRGGNVLPTQEPGYTVAESRQNPFGLIVALDNDG
KAQGSLYLDDGESLVVDSSLLVSFSVSDNTLSASPSGDYKADQPLANVTILGVGHKPKSVKFENANVDFTYKKSTVFVTGLDKYTK
DGAFSKDFTITW

Figure 22A

CAATTATCATTAATAATCACTCATGATCCCTGCGTCTAGAGGTTGGTCTAGACCACATCCGTGCACCAGACAAGACA
CGGCCCACGGAGGTAAAGGTGCCAACTCGCAAAGTGCAACAACCATGGCTCTCCAGCACGGTGCGTGGGGTAAAGAC
AATCTCCGGGAACCGATCCCGAAACCGAGAAAGAGGGTTTTAAGCGTGTGTCCTTTGCGGAGGCGGTGTAGCACTTC
TTATTGTCCTTTGGGCCGCTCCGGCGGTTGAGCTTCCACAGAACATCCTTGCACGGACAAGCAGTCCCGGAGACGCC
ATGTTGGGTGATACCCACTTCTGGCTGTACAGAGCTTTATATCACCTTACCTGGCGCTAGAGTAGACCCAATTCCCG
ACTCACACCACCCTCACATGCAGAACTAACCAATAAGGTAATTAATTAACACGATATAGCTCGTGGTGAACACTGGC
CCGGAGTAGTCATACGTGTAGGTTTTTGGCGTGATGAAAATCAGGTGGAGCACGACTTTTCGTAATGTTCGGGAGGG
AGTGCTGCAAACGGTATATAAGGACCAGTTTTTCTCGCAACATTATCAATTGCTCTTTAGTACAAAGATAATATAGA
AACAAATCTAGAATGGCGCACTCAATGTCTCGTCCCGTGGCTGCCACTGCCGCTGCTCTGTTGGCTCTGGCTCTTCC
CCAAGCTCTTGCCCAGGCCAACACCAGCTATGTCGATTACAACGTCGAGGCCAACCCTGACTTGTACCCTTTGTGCA
TAGAAACCATCCCACTGAGCTTCCCCGACTGCCAGAATGGCCCCCTGCGCAGCCACCTCATCTGCGACGAATCAGCC
ACCCCCTATGACCGAGCAGCATCGCTCATCTCGCTCTTCACGCTGGACGAGCTGATCGCCAACACCGGCAACACCGG
CCTCGGTGTCTCCCGACTGGGCCTCCCTGCATACCAAGTATGGAGTGAAGCACTTCACGGCCTCGACCGTGCCAACT
TCAGCGACTCAGGCTCCTACAATTGGGCTACTTCATTCCCCCAACCTATCTTGACCACCGCGGCCCTCAACCGCACC
CTCATTCACCAAATCGCCTCCATCATCTCCACCCAAGGCCGTGCCTTCAACAACGCCGGCCGCTACGGCCTCGATGT
CTACGCCCCCAACATCAACACCTTCCGCCACCCCGTCTGGGGTCGCGGACAAGAAACTCCAGGAGAGGACGTCTCTC
TCGCCGCCGTCTACGCCTACGAATACATCACCGGCATCCAGGGTCCCGACCCAGACTCAAACCTCAAACTTGCCGCC
ACGGCCAAGCACTACGCCGGCTATGACATCGAGAACTGGCACAACCACTCCCGCCTGGGCAATGATATGAACATCAC
CCAGCAAGACCTGTCAGAATACTACACTCCCCAGTTCCACGTCGCCGCCCGCGACGCCAAAGTCCACAGTGTCATGT
GTGCCTATAACGCCGTCGACGGCGTCCCTGCCTGCGCCGACTCTTACTTCCTCCAGACCCTCCTCCGCGACACCTTC
GGATTCGTTGACCACGGCTACGTCTCCAGCGACTGCGACGCCGCCTACAACATCTACAATCCCCACGGCTACGCCTC
CTCCCAGGCTGCCGCTGCCGCTGAGGCCATCCTCGCTGGCACTGACATCGACTGCGGTACCACCTACCAATGGCACC
TGAACGAGTCCATCACTGCGGGAGATCTCTCTCGCGATGATATCGAGAAGGGTGTGATCCGCCTCTACACGACCCTT
GTGCAGGCCGGATACTTCGACTCCAATACCACCAAGGCGAACAACCCCTACCGCGACCTCACCTGGTCCGATGTCCT
CGAGACGGACGCATGGAACATCTCCTACCAAGCCGCGACGCAGGGCATTGTCCTTCTCAAGAACTCCAACAACGTCC
TTCCCCTCACCGAGAAAGCTTACCCACCATCCAACACCACCGTCGCCCTTATCGGTCCCTGGGCCAACGCCACCACC
CAACTCCTGGGCAACTACTACGGCAACGCTCCCTACATGATCAGCCCCCGCGCCGCGTTCGAAGAAGCCGGATACAA
AGTCAACTTCGCCGAAGGCACCGGTATCTCCTCCACAAGCACCTCGGGCTTCGCAGCCGCCTTATCCGCCGCCCGGT
CCGCCGACGTGATCATCTACGCCGGTGGTATCGACAATACTCTTGAAGCGGAGGCACTGGATCGCGAGAGCATCGCA
TGGCCGGGTAACCAACTGGACTTGATCCAAAAGCTCGCCTCGTCGGCCGGAAGCAAGCCGCTCATCGTTCTCCAAAT
GGGCGGCGGACAGGTCGATTCCTCGTCCCTCAAGAACAACACGAACGTCACTGCACTCCTCTGGGGCGGATACCCCG
GCCAATCCGGCGGTTTCGCTCTGAGAGACATCATCACGGGAAAGAAGAACCCCGCGGGTAGACTAGTCACGACACAA
TACCCAGCCAGCTACGCGGAGGAGTTCCCCGCGACGGATATGAACCTCCGTCCTGAGGGTGATAACCCCGGCCAAAC
ATACAAATGGTACACCGGCGAAGCAGTGTACGAGTTCGGCCACGGATTATTCTACACGACCTTCGCGGAATCATCCA
GCAACACCACTACGAAGGAAGTTAAGCTCAACATCCAGGACATTCTTTCCCAGACACACGAAGAGCTAGCCTCAATT
ACGCAGCTCCCTGTGCTGAACTTCACTGCCAATATCAAGAACACTGGAAAGCTGGAATCGGATTACACCGCTATGGT
ATTCGCCAATACCTCTGATGCCGGTCCGGCGCCGTACCCGGTGAAGTGGCTGGTCGGGTGGGATCGGCTTGGGGATG
TGAAGGTCGGGGAGACGAGGGAGTTGAGGGTTCCCGTTGAGGTGGGGAGCTTTGCGAGGGTGAATGAGGATGGCGAT
TGGGTGTTGTTTCCGGGAACGTTTGAGTTGGCGTTGAACCTGGAGAGGAAGGTTAGGGTGAAGGTTGTTCTTGAGGG
TGAGGAGGAAGTCGTGCTGAAGTGGCCTGGGAAGGAGTAG<u>AAAATACTATTCTGTTGATGGCTCTAGGGGATGAGAG</u>
<u>TCAGCCTATTACTGGATATGCATAGTGGTGATACGATGTATATAGCTCTATGAAGTAATTAGTTCAAGTGGGAATAC</u>
<u>CCCTTTCACACATATAGTATGCTGTTATTCCGAAATAGGGATCATTTCTGATTAATAGTAGCGGTAGCGATGGTCAC</u>
<u>ACACGACTTAATGTTCCCCATTGTACCGGAAGTAACAATTCCAGTGACCTCTTAGAAGAAAGACAGCAAGAAAAAGT</u>
<u>AAGAAAGGCAAATTGATCAAAAATAAGGCCATCTACAGCCTATTCACATTTAGCCGGATCTGCAATACAGCTACAG</u>
<u>AAATAAGTTTGTTAGGCTGCTTGCTAGCATAGCT</u>

Figure 22B

MAHSMSRPVAATAAALLALALPQALAQANTSYVDYNVEANPDLYPLCIETIPLSFPDCQNGPLRSHLICDESATPYD
RAASLISLFTLDELIANTGNTGLGVSRLGLPAYQVWSEALHGLDRANFSDSGSYNWATSFPQPILTTAALNRTLIHQ
IASIISTQGRAFNNAGRYGLDVYAPNINTFRHPVWGRGQETPGEDVSLAAVYAYEYITGIQGPDPDSNLKLAATAKH
YAGYDIENWHNHSRLGNDMNITQQDLSEYYTPQFHVAARDAKVHSVMCAYNAVDGVPACADSYFLQTLLRDTFGFVD
HGYVSSDCDAAYNIYNPHGYASSQAAAAAEAILAGTDIDCGTTYQWHLNESITAGDLSRDDIEKGVIRLYTTLVQAG
YFDSNTTKANNPYRDLTWSDVLETDAWNISYQAATQGIVLLKNSNNVLPLTEKAYPPSNTTVALIGPWANATTQLLG
NYYGNAPYMISPRAAFEEAGYKVNFAEGTGISSTSTSGFAAALSAARSADVIIYAGGIDNTLEAEALDRESIAWPGN
QLDLIQKLASSAGSKPLIVLQMGGGQVDSSSLKNNTNVTALLWGGYPGQSGGFALRDIITGKKNPAGRLVTTQYPAS
YAEEFPATDMNLRPEGDNPGQTYKWYTGEAVYEFGHGLFYTTFAESSSNTTTKEVKLNIQDILSQTHEELASITQLP
VLNFTANIKNTGKLESDYTAMVFANTSDAGPAPYPVKWLVGWDRLGDVKVGETRELRVPVEVGSFARVNEDGDWVLF
PGTFELALNLERKVRVKVVLEGEEEVVLKWPGKE

Figure 23A

CAATTATCATTAATAATCACTCATGATCCCTGCGTCTAGAGGTTGGTCTAGACCACATCCGTGCACCAGACAAGACAC
GGCCCACGGAGGTAAAGGTGCCAACTCGCAAAGTGCAACAACCATGGCTCTCCAGCACGGTGCGTGGGGTAAAGACAA
TCTCCGGGAACCGATCCCGAAACCGAGAAAGAGGGTTTTAAGCGTGTGTCCTTTGCGGAGGCGGTGTAGCACTTCTTA
TTGTCCTTTGGGCCGCTCCGGCGGTTGAGCTTCCACAGAACATCCTTGCACGGACAAGCAGTCCCGGAGACGCCATGT
TGGGTGATACCCACTTCTGGCTGTACAGAGCTTTATATCACCTTACCTGGCGCTAGAGTAGACCCAATTCCCGACTCA
CACCACCCTCACATGCAGAACTAACCAATAAGGTAATTAATTAACACGATATAGCTCGTGGTGAACACTGGCCCGGAG
TAGTCATACGTGTAGGTTTTTGGCGTGATGAAAATCAGGTGGAGCACGACTTTTCGTAATGTTCGGGAGGGAGTGCTG
CAAACGGTATATAAGGACCAGTTTTTCTCGCAACATTATCAATTGCTCTTTAGTACAAAGATAATATAGAAACAAACA
TATGGTTGCCTTTTCCAGCCTCATCTGCGCTCTCACCAGCATCGCCAGTACTCTGGCGATGCCCACAGGCCTCGAGCC
TGAGAGCAGTGTCAACGTCACAGAGCGTGGCATGTACGACTTTGTTCTTGGAGCTCACAATGATCATCGCCGTCGTGC
TAGCATCAACTACGACCAAAACTACCAAACTGGCGGACAAGTCAGCTATTCGCCTTCCAACACTGGCTTCTCAGTGAA
CTGGAACACTCAAGATGACTTTGTTGTGGGCGTTGGTTGGACGACTGGATCTTCTGCTCCCATCAACTTTGGCGGCTC
TTTTAGTGTCAACAGCGGAACTGGCCTGCTTTCCGTCTATGGCTGGAGCACCAACCCACTGGTTGAGTACTACATCAT
GGAGGACAACCACAACTACCCAGCACAGGGTACCGTCAAGGGAACCGTCACCAGCGACGGAGCCACTTACACCATCTG
GGAGAATACCCGTGTCAACGAGCCTTCCATCCAGGGCACAGCGACCTTCAACCAGTACATTTCCGTGCGGAACTCGCC
CAGGACCAGCGGAACTGTTACTGTGCAGAACCACTTCAATGCTTGGGCCTCGCTTGGCCTGCACCTTGGGCAGATGAA
CTACCAGGTTGTCGCTGTCGAAGGCTGGGGTGGTAGTGGTTCTGCCTCACAGAGTGTCAGCAACTAGAGCTTGGAGAC
GTGGAAGGACATACCGCTTTTGAGAAGCGTGTTTGAAAATAGTTCTTTTTCTGGTTTATATCGTTTATGAAGTCATCA
GATGAAAAGCTGAAATAGCGAGTATAGGAAAATTTAATGAAAATTAAATTAAATATTTTCTTAGGCTATTAGTCACCT
TCAAAATGCCGGCCGCTTCTAAGAACGTTGTCATGATCGACAACTACGACTCGTTTACCTGGAACCTGTACGAGTACC
TGTGTCAGGAGGGAGCCAATGTCGAGGTTTTCAGGAACGATCAGATCACCATTCCGGAGATTGAGCAGCTCAAGCCGG
ACGTTGTGGTGATATCCCCTGGTCCTGCCCATCCAACAACAGACTCGGGAATATCTCGCGACGTGATCAGCCATTTTA
AAGGCAAGATT

Figure 23B

MVAFSSLICALTSIASTLAMPTGLEPESSVNVTERGMYDFVLGAHNDHRRRASINYDQNYQTGGQVSYSPSNTGFSV
NWNTQDDFVVGVGWTTGSSAPINFGGSFSVNSGTGLLSVYGWSTNPLVEYYIMEDNHNYPAQGTVKGTVTSDGATYT
IWENTRVNEPSIQGTATFNQYISVRNSPRTSGTVTVQNHFNAWASLGLHLGQMNYQVVAVEGWGGSGSASQSVSN

DEVELOPMENT OF STRAINS OF THE THERMOTOLERANT YEAST *HANSENULA POLYMORPHA* CAPABLE OF ALCOHOLIC FERMENTATION OF STARCH AND XYLAN BY EXPRESSION OF STARCH AND XYLAN DEGRADING ENZYMES

PRIORITY AND INCORPORATION BY REFERENCE

This application claims priority to U.S. provisional application No. 61/050,685 filed May 6, 2008, which is incorporated by reference in its entirety, including all references cited therein (repeated herein) to the extent such references aid in understanding the invention or in obtaining the materials and methods that would facilitate the practice of the invention. If the content of a cited reference conflicts with teaching of the present application, the present application shall be deemed the controlling understanding.

TECHNICAL FIELD

This application relates to the field of cellulosic ethanol production by fermentation, particularly to fermentation of starch and xylan carbon sources, still more particularly to recombinant *H. polymorpha* strains useful for the production of ethanol by fermentation on starch and xylan, and still more particularly to strains of *H. polymorpha* that excrete recombinant a amylase and glucoamylase, and/or xylohydrolase and xylosidase to achieve ethanol production by fermentation on starch and xylan containing media.

INTRODUCTION

Fuel ethanol production from renewable raw materials, such as plant biomass, is of great economic and ecological significance. Plant lignocellulosics have the potential as alternative feedstocks to sucrose and starch-based polysaccharides that are currently widely in use for bioethanol production. Lignocellulocis and other plant derived polysaccahrides represent a renewable sustainable energy resource that can be reproduced by the bioconversion of carbon dioxide. One of the many touted environmental benefits of biofuels produced from plants over fossil fuels is the significant reduction in greenhouse gases [6, 24].

Most ethanol produced in the world today is derived from starch or sucrose. Starches and sugars are abundant in many crops, but expansion of ethanol production as a liquid transportation fuel will require feedstocks that do not compete directly with food or animal feed uses. Such feedstocks include lignocellulosic byproduct residues from agriculture and silviculture [14].

Lignocellulose is a generic term for plant matter derived from wood and agricultural residues. It is composed mainly of lignin and cellulose as well as significant amounts of hemicellulose with lesser quantities of structural proteins and organic solvent extractable matter [14]. Hemicellulose is a substituted polysaccharide that consist of xylan as the backbone and is present in plant cell walls [11].

Processing of lignocellulosics and starch to ethanol consists of four major unit operations: pretreatment, hydrolysis, fermentation, and product separation/purification. Bioconversion of the starch involves enzymatic hydrolysis and fermentation of the resulting glucose to ethanol with the production of animal feed co-products. Hydrolysis of lignocellulose is more difficult by reason of its more complex structure and the great variation in its composition in different plants (cereals, softwoods, hardwoods, etc.) and within a plant (stems, hulls, straws, cobs, stover, leaves, kernels, etc.) [14]. Xylose is the major pentose sugar obtained upon hydrolysis of the hemicellulose fraction with the CS L-arabinose and other C6 sugars such as glucose, mannose, galactose as the primary hexoses [11].

Due to the many steps involved and the high energy inputs required to process of lignocellulosics, the development of more direct and less expensive technologies are needed for commercial viability of lignocelluloscis as feedstocks. The direct microbial conversion (DMF, Direct Microbial Fermentation) of carbohydrate polymers is one option that can improve the economics of bioethanol production from lignocellulosics. One of the key prerequisites for development of this technology is obtaining microorganisms capable of direct starch and xylan fermentation to ethanol at elevated temperatures [15]. The optimal temperature of the current hydrolytic enzymes involved in DMF is approximately 50° C. whereas most of the microorganisms currently used for bioethanol production from lignocellulosic and starchy sugars are mesophiles with optimum of growth and fermentation temperatures between 28 and 40° C. [6].

Recent studies in our lab indicate that the thermotolerant methylotrophic yeast, *Hansenula polymorpha*, is able to ferment D-xylose and D-glucose to ethanol at elevated temperatures (37-48° C.). In view of its high optimum temperature for growth and fermentation, *H. polymorpha* is a good candidate for further development of DMF technology [3, 26]. Since *H. polymorpha* cannot utilize starch and xylan as carbon and energy sources, the cloning and overexpression of heterologous xylanolytic and amylolytic genes in this yeast is necessary.

β-1,4-xylans are heterogeneous polysaccharides found in almost all parts of cell wall of plants. The β-1,4-linked xylose monomers form a backbone chain to which several substituents are attached [30]. Hydrolysis of the xylan backbone is catalyzed by endo-β-1,4-xylanases (1,4-beta-D-xylan xylanohydrolase, EC 3.2.1.8) and β-D-xylosidases (1,4-beta-D-xylan xylohydrolase, EC 3.2.1.37). Endo-β-xylanases act on xylans and xylooligosaccharides, producing mainly mixtures of xylooligosaccharides. β-D-Xylosidases hydrolyze xylo-oligosaccharides to D-xylose [19]. The fungi *Trichoderma* and *Aspergillus* secrete large amounts of efficient xylan-degrading enzymes. *Trichoderma reesei* is a filamentous mesophilic fungus known for its cellulolytic and xylanolytic activities [3]. The two major inducible endo-xylanases secreted by this fungus are Xyn1 and Xyn2. Xyn2 represents more than 50% of the total xylanolytic activity of *T. reesei* cultivated on xylan. Members of the genus *Aspergillus* are also efficient producers of cellulolytic and xylanolytic enzymes. The xlnD gene of *A. niger* encoding the 804-amino acid β-xylosidase was successfully expressed in yeast [19].

Starch is composed of two high molecular weight fractions: amylose and amylopectin. Amylose, the minor component (20-30%) is a linear polysaccharide formed by α-1,4-linked glucose residues and some α-1,6-branching points, while amylopectin represents the major fraction of starch (70-80%) and is highly branched [4]. Starch is degraded by two secreted amylases: α-amylase and a glucoamylase [25]. α-Amylase (1,4-α-D-glucan glucanohydrolase, EC 3.2.1.1) catalyzes the endoamylolytic cleavage of α-1,4-glucosidic linkages of starch and similar substrates releasing maltose, oligosaccharides and limit dextrins. Glucoamylase (1,4-α-D-glucanglucohydrolase, EC 3.2.1.3) hydrolyzes glucooligosaccharides and maltose to D-glucose. The yeast *Schwanniomyces occidentalis* produces amylolytic enzymes and ferments starch to ethanol with high efficiency [34]. The α-Amylase secreted by this yeast is encoded by SWA2 gene. The GAM1 gene encodes the secretory glucoamylase.

Some agricultural lignocellulosic residues obtained from the processing of cereal grains such as corn (example: corn fiber hulls) contain a significant quantity of starch. For this reason developing microbial strains capable of active direct conversion of both starch and lignocellulose to ethanol is of great economical significance.

SUMMARY

Described herein are amylolytic and xylanolytic strains of *H. polymorpha* capable of direct alcoholic fermentation of starch and xylan. Here we describe construction of the strains by successful insertion into the chromosome and expression of the genes *Scw. occidentalis* SWA2 and GAM1, *T. reesei* XYN2 and *A. niger* xlnD in this yeast. Also, a strain that over expresses pyruvate decarboxylase (PDC) was engineered with one or more of these genes. In each case the strains were able to grow solely on media containing either solubilized starch or solubilized xylan and were able to ferment the same into ethanol at various levels. The strains that also over expressed PDC gave higher ethanol titers than strains that only overexpressed the SWA2 and GAM1 genes.

DESCRIPTION OF THE DRAWINGS

FIG. 17. Growth of the *H. polymorpha* recombinants expressing endoxylanase and β-xylosidase genes on the medium with xylan as sole carbon source. A, Growth of the recombinant strains expressing endoxylanase and β-xylosidase genes (strains ##6× and 8×) on the solid medium with xylan as sole carbon source. B, Biomass accumulation by the strains expressing endoxylanase and β-xylosidase genes during growth in the liquid minimal medium with 3% xylan from birchwood (B1) or 2% xylose (B2), 48° C., 240 rpm. 6×, 8×, the transformants 495 2Eth⁻ leu1-1/pOR2.

FIG. 20. A. Sequence of a recombinant construct containing the *H. polymorpha* GAP promoter (single underscore) operably linked to a SWA2 gene (SEQ. ID NO 1) and to the *H. polymorpha* AOX terminator (double underscore). B. Amino acid sequence of the α-amylase (SEQ. ID NO2) from *Schwanniomyces occidentalis* encoded by the SWA2 gene.

FIG. 21. A. Sequence of a recombinant construct containing the *H. polymorpha* GAP promoter (single underscore) operably linked to a GAM1 gene (SEQ. ID NO 3) and to the *H. polymorpha* AOX terminator (double underscore). B. Amino acid sequence of the glucoamylase (SEQ. ID NO 4) from *Schwanniomyces occidentalis* encoded by the GAM1 gene.

FIG. 22. A. Sequence of a recombinant construct containing the *H. polymorpha* GAP promoter (single underscore) operably linked to an xlnD gene (SEQ. ID NO 5) of *A. niger* including its endogenous terminator sequence (SEQ. ID NO 9, double underscore). B. Amino acid sequence of the β-xylosidase (SEQ. ID NO 6) encoded by the xlnD gene.

FIG. 23. A. Sequence of a recombinant construct containing the *H. polymorpha* GAP promoter (single underscore) operably linked to an Xyn2 gene (SEQ. ID NO 7) from *Trichoderma reesei* including its endogenous terminator sequence (SEQ. ID NO 10, double underscore). B. Amino acid sequence of the endo-β-xylanase (SEQ. ID NO 8) encoded by the Xyn2 gene.

DETAILED DESCRIPTION OF METHODS, STRAINS, AND RESULTS

Strains and Media

The *H. polymorpha* strain 495 2Eth⁻ leu1-1 deficient in β-isopropylmalate dehydrogenase and unable to grow on ethanol [14], was used as a recipient for isolation of the amylolytic and xylanolytic recombinants. This strain is a derivative of NCYC 495 leu1-1 [8]. Yeast strains and transformants were grown on YPD (0.5% yeast extract, 1% peptone, 2% glucose) or minimal medium (0.67% YNB without amino acids, 2% glucose, 3% soluble starch (Sigma S2630-500G) or 3% xylan from birchwood (Fluka X0502-100G) at 37° C. or 48° C. For the 495 2Eth⁻ leu1-1 strain, leucine (40 mg/L) was added to the medium. For the selection of yeast transformants on YPD, 0.2 mg/L of G418 (geneticin) or 150 µg/ml of zeocine were added.

The *E. coli* DH5α strain [Φ80dlacZΔM15, recA1, endA1, gyrA96, thi-1, hsdR17(r⁻$_K$, m⁺$_K$), supE44, relA1, deoR, Δ(lac-ZYA-argF)U169] was used as a host for propagation of plasmids. The strain was grown at 37° C. in LB medium as described previously [27]. Transformed *E. coli* cells were maintained on a medium containing 100 mg/L of ampicillin.

DNA Techniques

Standard cloning techniques were applied [27]. Plasmid DNA isolation from *E. coli* was performed with the Wizards Plus SV Minipreps DNA Purification System (Promega, Madison, Wis., USA). Genomic DNA of *H. polymorpha*, *Scw. occidentalis*, *T. reesei* and *A. niger* was isolated using the Wizards Genomic DNA Purification Kit (Promega, Madison, Wis., USA). Restriction endonucleases, T4 DNA ligase and T4 DNA polymerase (Fermentas, Vilnius, Lithuania) were used according to the manufacturer specifications. DNA fragments were separated on 0.8% agarose (Fisher Scientific, Fair Lawn, N.J., USA) gel in 1×TAE [27]. Isolation of fragments from the gel was carried out with a DNA Gel Extraction Kit (Millipore, Bedford, Mass., USA). Taq DNA polymerase and High Fidelity Mix Polymerase (both Fermentas, Vilnius, Lithuania) were used for analytical and preparative PCR, respectively. PCRs were performed in GeneAmps PCR System 9700 thermocycler (Applied Biosystems, Foster City, Calif., USA). Transformation of the yeast *H. polymorpha* by electroporation was carried as described before [5].

Construction of Plasmids Carrying the α-Amylase and Glucoamylase Genes of *Scw. occidentalis*

Figure 1:
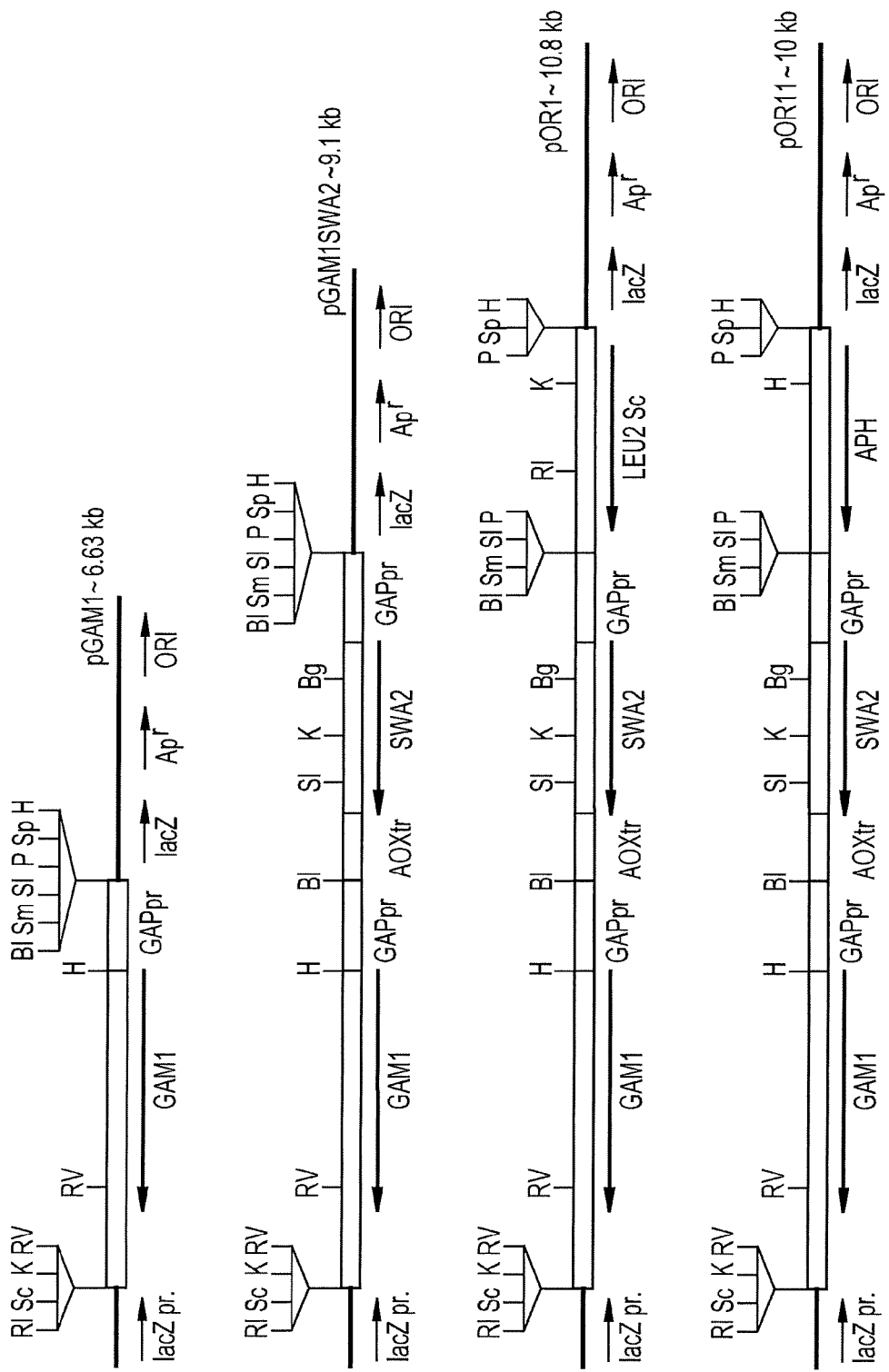
FIG. 1. Linear schemes of the plasmids pGAM1 (~6.63 kb), pGAM1SWA2 (~9.1 kb), pOR1 (~10.8 kb) and pOR11 (~10 kb). The *S. cerevisiae* genome fragment containing the LEU2 gene is shown as grey box, the HpGAP promoter is shown as green box, the HpAOX terminator: orange box, the ORF of the GAM1 gene is shown as blue box, the ORF of the SWA2 gene: red box, the aminoglycoside 3-phosphotransferase gene (APH): black box. Restriction sites: H, Hind III; RV, EcoRV; K, Kpn I; RI, EcoR I; Si, Sal I; BI, BamH I; Bg, Bgl II; Sc, Sac I; P, P st I; Sm, Sma I.

The open reading frame (ORF) together with native terminator of the GAM1 gene encoding glucoamylase (~3.27 kb) was isolated from the genomic DNA of the *Schw. occidentalis* strain NRRL Y-2470 by PCR using primers Ko48 (CCC AAGCTTATG ATT TTT CTG AAG CTG) and Ko49 (GGA AGATCTTTC TTT ACA AGA CCA ATG). Restriction sites Hind III and Bgl II were incorporated into the primers Ko48 and Ko49 (the cleavage sites are underlined). The PCR product was digested with Hind III and Bgl II restriction endonucleases and put under the strong constitutive promoter of glyceraldehyde-3-phosphate dehydrogenase gene (HpGAPpr), digested with Hind III and Bam HI. The construct HpGAPpr+GAM1 was inserted into the Bam HI site of the plasmid pUC57 by means of double ligation. The resulting plasmid was named pGAM1 and used as a vector for the following constructions (FIG. 1).

Figure 2:
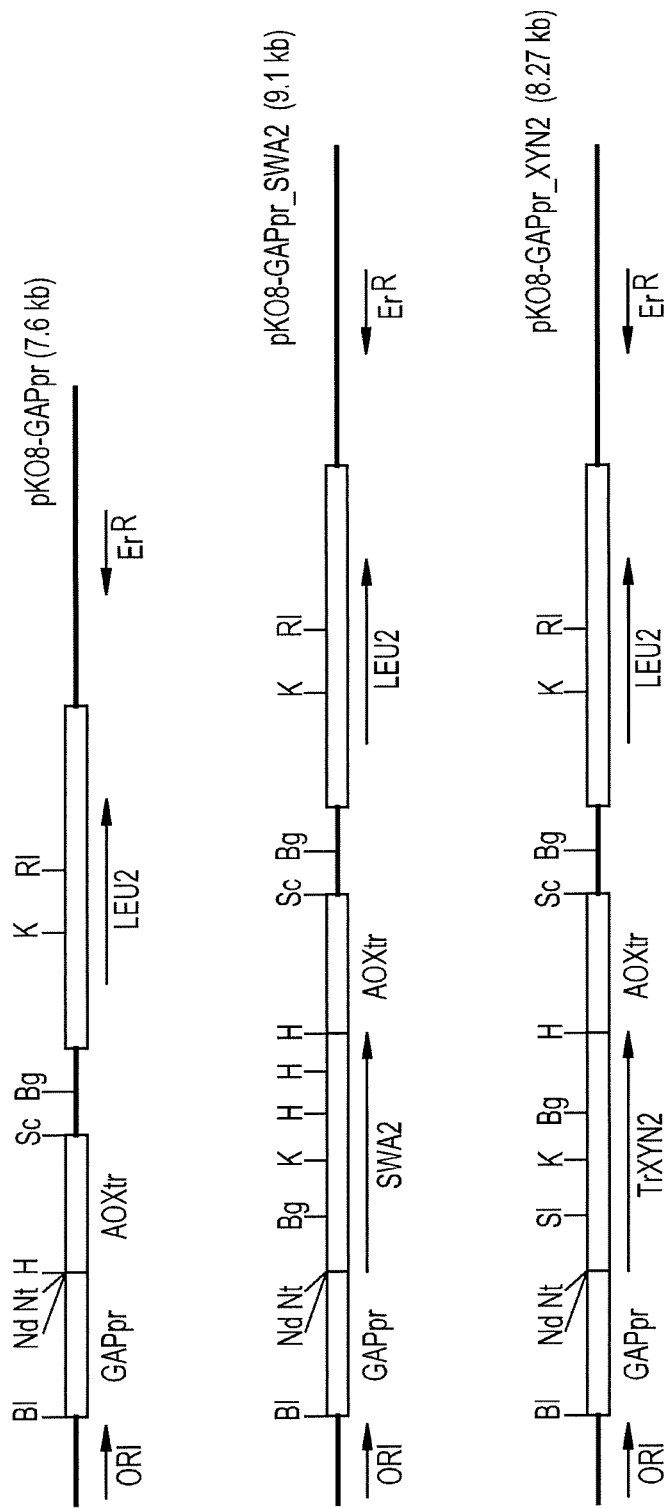
FIG. 2. Linear schemes of the plasmids pKO8-GAPpr (7.6 kb), pKO8-GAPpr_SWA2 (9.1 kb) and pKO8-GAPpr_XYN2 (8.27 kb). The *S. cerevisiae* genome fragment containing the LEU2 gene is shown as grey box, the HpGAP promoter is shown as yellow box, the HpAOX terminator: blue box, the ORF of the SWA2 gene: red box, the ORF of TrXYN2 gene: orange box. Restriction sites: H, Hind III; Nd, Nde I; K, Kpn I; RI, EcoR I; Sl, Sal I; BI, BamHI; Bg, Bgl Sc, Sac I; P, Pst I; Nt, Not I.

ORF of the SWA2 gene encoding α-amylase (~2 kb) was amplified by PCR using primers SWA1 (TAG TCG CATATGAG ATT TTC AAC TGA AGG), SWA2 (CTA TTG ATT GCA GAT GCC AGA TCC C) and genomic DNA of *Scw. occidentalis* NRRL Y-247 as a template. The Nde I restriction site was incorporated into the SWA1 primer. 5'-end of the PCR product was digested with Nde I, whereas 3'-end was blunted. The product was inserted into the plasmid pKO8-GAPpr (FIG. 2). ORF of the SWA2 gene was put under the HpGAPpr and fused with the HpAOX terminator (HpAOXtr). The constructed plasmid pKO8-GAPpr_SWA2 was used as a template for amplification by PCR of the DNA fragment containing HpGAPpr+SWA2_ORF+HpAOXtr using primers K43 (CCGGATCCC AAT TAT CAT TAA TAA TC), Ko51 (CGC GGATCCAAT CTT GCC ITT AAA ATG). The resulting PCR product was digested with Bam HI restriction endonuclease and inserted into the Bam HI site of the plasmid pGAM1. The constructed plasmid was named pGAM1SWA2 (FIG. 1). The *Saccharomyces cerevisiae* LEU2 gene (selection marker) was inserted into the Pst I restriction site of the plasmid pGAM1SWA2 and resulting construct was named pOR1 (FIG. 1).

The aminoglycoside 3-phosphotransferase gene (APH) conferring resistance to G418 in yeasts was isolated from the plasmid pGLG61 after its digesting by Pst I restriction endonuclease. The Pst I-fragment of pGLG61 [30] containing the gene was ligated with Pst I-portion of the plasmid pOR1 carrying recombinant genes GAM1, SWA2 and bacterial part, but without the *S. cerevisiae* LEU2 gene. Resulting plasmid was named pOR11 (FIG. 1).

The sequence of the SWA2 and GAM1 recombinant constructs for expression in *H. polymorpha* are shown in FIGS. 20 and 21 respectively.

Construction of Plasmids Carrying the Endoxylanase and β-xylosidase Genes of *T. reesei* and *A. niger*, Respectively The gene xlnD coding for β-xylosidase was derived from the fungus *A. niger*. ORF of the xlnD gene together with the native terminator (~2.79 kb) was isolated from the genomic DNA of the *A. niger* strain NRRL 3 using primers Ko46 (TGC TCTAGAATG GCG CAC TCA ATG TCT CG) and Ko47 (CCC GAGCTCAGC TAT GCT AGC AAG CAG C). The PCR product was treated with Sac I and Xba I restriction endonucleases (the sites of these endonucleases flank the product) and put under the HpGAPpr. The construct HpGAPpr+xlnD was inserted into the SacI site of the plasmid pUC57. The resulting plasmid was named pxlnD and used as a vector for the following constructions (FIG. 3).

ORF of the XYN2 gene encoding endoxylanase (~0.67 kb) without intron region was amplified by PCR using primers TR1 (TTC TCA CATATGGTT GCC TTT TCC AGC CCT CAT CTG CGC), TR2 (CTA GTT GCT GAC ACT CTG TGA GGC AGA ACC ACT ACC ACC), TRir (GAG CCG CCA AAG TTG ATG GGA GCA GAA GAT CCA GTC GTC), TRif (GAC GAC TGG ATC TTC TGC TCC CAT CAA CTT TGG CGG CTC) and genomic DNA of *T. reseei* NRRL 11460 as a template. 5'-end of the PCR product was digested with Nde I, whereas 3'-end was blunted. The product was inserted into the plasmid pKO8-GAPpr (FIG. 2). ORF of the XYN2 gene was put under the HpGAPpr and terminated by the HpAOXtr. The resulting plasmid pKO8-GAPpr_XYN2 (FIG. 2) was used as a template for amplification by PCR of the DNA fragment containing HpGAPpr+ORF_XYN2+HpAOXtr using primers K43 (CCGGATCCC AAT TAT CAT TAA TAA TC), Ko50 (GGA AGATCTAAT CTT GCC TTT AAA ATG). The resulting PCR product was digested with restriction endonucleases Bam HI and Bgl II and inserted into the Bam HI site of the plasmid pxlnD. The constructed plasmid was named pxlnDXYN2 (FIG. 3).

Figure 3:
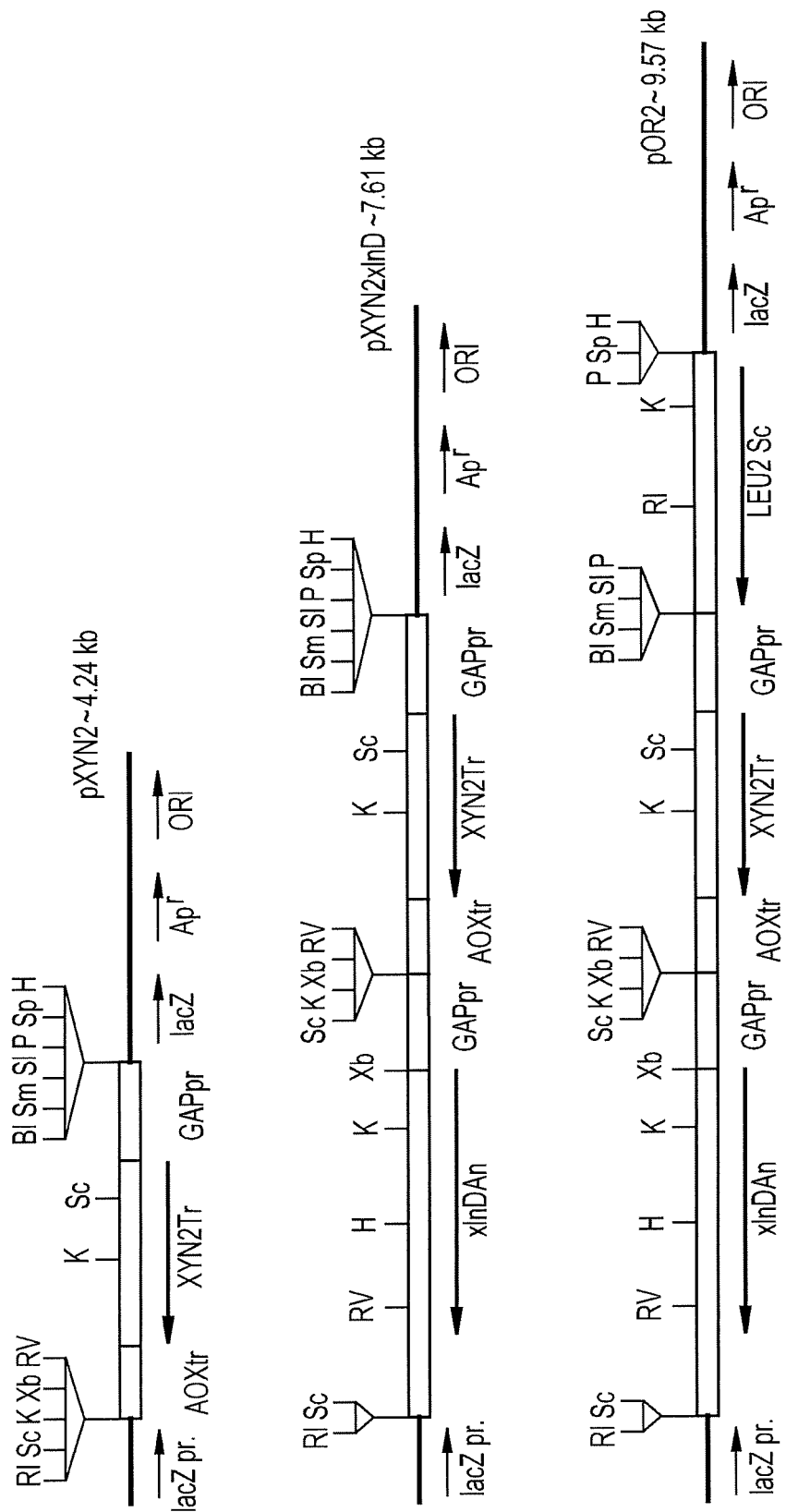
FIG. 3. Linear schemes of plasmids pXYN2 (~4.24 kb), pXYN2xlnD (~7.61 kb) and pOR2 (~9.57 kb). Grey box, the *S. cerevisiae* genome fragment containing the LEU2 gene; green box, the HpGAP promoter; orange box, the HpAOX terminator; blue box, the fragment containing ORF of *A. niger* xlnD gene; red box, the fragment containing ORF of *T. reseei* gene XYN2. Restriction sites: H, Hind III; RV, EcoRV; K, Kpn I; RI, EcoR I; Sl, Sal I; B, BamH I; Bg, Bgl II; Sc, Sac I; P, P st I; Sm, Sma I; Xb, XbaI; Sp, Sph I.

The *S. cerevisiae* LEU2 gene was inserted into the Pst I site of the plasmid pxlnD XYN2 and the final plasmid was designated as pOR2 (FIG. 3).

The sequence of the XylD and XYL2 recombinant constructs for expression in *H. polymorpha* are shown in FIGS. 22 and 23 respectively.

Screening for Amylase Activity

Recombinant strains obtained after transformations with plasmids carrying genes of α-amylase and glucoamylase were screened for amylolytic activity after plating on minimal medium containing 2% soluble starch (Sigma) as a carbon source. Plates were incubated at 37° C. for 2 days followed by holding at 4° C. overnight. Amylolytic clones were detected by clear halos around colonies [4, 16].

Screening for Endoxylanase Activity

Corresponding transformants were screened for xylan-degrading ability after being plated on a minimal medium containing 0.2% of 4-O-methyl-D-glucurono-D-xylan-remazol brilliant blue R (RBB)-xylan (Sigma) and 2% glucose as carbon source. Plates were incubated at 37° C. for 3-4 days. Endoxylanase cleaves RBB-xylan into a colorless product forming clear halos around the colonies [11, 20].

Screening for β-Xylosidase Activity

Corresponding transformants were screened for β-xylosidase activity after being plated on a minimal medium containing 1 mM p-nitrophenyl-β-D-xyloside (PNPX) and 2% glucose as a carbon source. Plates were incubated at 37° C. for 1-3 hours. Enzyme activity was detected by production of yellow halos around the colonies [19].

α-Amylase and Glucoamylase Activity Assays

Appropriate dilutions of the cell-free culture were used for enzymes assays.

Total amylase activity was measured using the 3,5-dinitrosalicylic acid (DNS) method. A 50 μl aliquot of culture supernatant was incubated with 200 μl of 0.4M sodium acetate buffer (pH 5.0) containing 2% soluble starch for 30 min at 50° C. The mixture was boiled for 10 min to stop the reaction. One unit of α-amylase activity was defined as the amount of enzyme required to release 1 μmol of reducing sugar per ml per min under the same culture conditions [17, 22].

In the assay of glucoamylase activity, after keeping 0.9 ml of the starch solution boiled in sodium acetate buffer (pH 5.5) at 30° C. for 5 min, 0.1 ml of the sample was added and the mixture was incubated for 15 min. The reaction was then stopped by boiling the reaction mixture for 10 min and the concentration of glucose produced was determined using the "Diagluc" assay kit (UBT, Lviv, Ukraine) [9]. Activity of α-amylase was calculated by subtracting glucoamylase activity from total amylase activity. One unit of glucoamylase activity was defined as the amount of enzyme required to release 1 μmol of glucose per mM from substrate [28].

β-Xylosidase and Endoxylanase Activity Assays

Enzyme producing cultures were grown in 3 ml YPD overnight. Cells were collected by centrifugation and supernatant was used for enzymes activity measuring.

Endo-β-1,4-xylanase activity was assayed by the method described by Bailey et al. [1] with 1% birchwood xylan (Fluka) as the substrate at 50° C. Appropriate dilutions of the cell-free culture solution in 50 mM sodium citrate buffer (pH 5.0) were used as the enzyme source. The amount of released sugar was determined by the dinitrosalicylic acid method [20]. The β-xylosidase activity was quantified using the chromophoric substrate PNPX at concentration of 5 mM. The supernatant was used as source of β-xylosidase for the activity determination assays. All activities were expressed in kat/ml; one katal is the amount of enzyme needed to produce 1 mol of reducing sugar from birchwood xylan or chromophoric substrate per second [19].

Ethanol Production Assay

For ethanol production, *H. polymorpha* transformants were grown during 4 days in a liquid minimal medium containing 3% soluble starch or 3% xylan from birchwood at 48° C., in semi-aerobic conditions. Concentrations of ethanol in the medium were determined after every 24 hr using the "Alcotest" kit [10].

Effects of pH and Aeration on Effectiveness of Fermentation of Starch to Ethanol Optimal conditions for the direct fermentation of starch into ethanol by isolated transformants were studied. Yeast strains were pre-cultured at 48° C. in 50 ml of YPD medium in 125 ml Erlenmeyer flasks for 48 hours with agitation set at 220 rpm in the shaker Inkubator 1000 Heidolph (Schwabach, Germany). The cells were inoculated at concentration of 2 mg/ml into 50 ml of the minimal medium containing 3% potato soluble starch as sole carbon source.

Figure 4A:
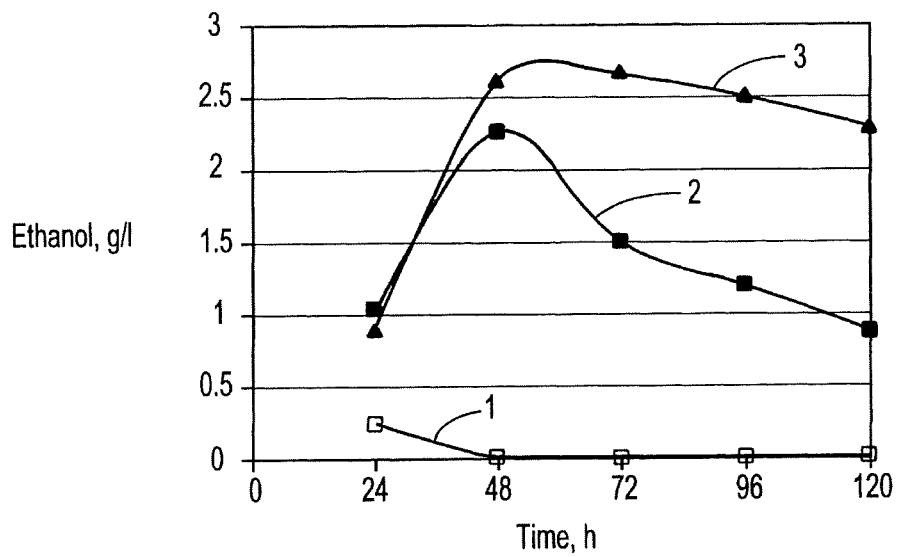
FIG. 4. Ethanol production by the *H. polymorpha* recombinants 2Eth⁻ leu1-1/pOR1 #14' (A) and #7 (B) in the minimal YNB medium with the 2% soluble starch as sole carbon source with different medium pH: 1—without pH adjacent; 2—pH 6; 3—pH 5.5; 48° C., 135 rpm.
Figure 4B:
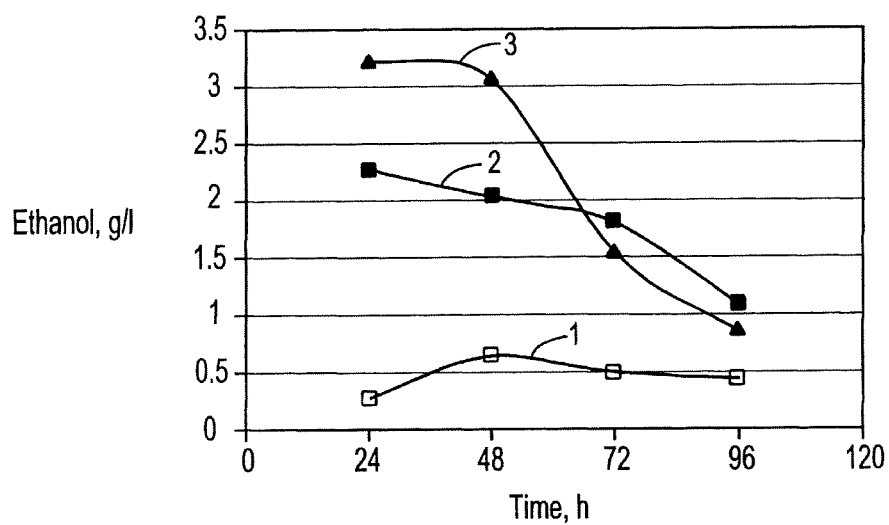

The effect of pH of the medium on ethanol production during starch fermentation was investigated. The optimum pH for α-amylase is ~6.0 and for glucoamylase is 5.2-5.5. The fermentation was carried out using media with pH 5.5 and 6.0. A 1 M potassium phosphate buffer was used for adjusting the medium pH. The best ethanol production was in the medium with pH 5.5 (FIGS. 4 A & B).

Effect of aeration on the fermentation efficiency was studied. Rotation rates from 120 to 180 rpm were tested. The highest ethanol production was in the case of the 135 rpm rotation.

Effects of pH, Aeration and Substrate Concentration on Effectiveness of Fermentation of Xylan to Ethanol Optimal conditions for the fermentation of birchwood xylan to ethanol by isolated transformants were studied. The yeast strains were pre-cultured at 48° C. in 50 ml of YPD medium in 125 ml Erlenmeyer flasks for 48 hours with agitation set at 220 rpm. Cells were removed by centrifugation at 4000 rpm for 5 min, washed and inoculated (at concentration of 2 mg/ml) into 50 ml of a minimal medium containing 3% or 9% birchwood xylan and 0.05% of glucose as carbon sources.

Figure 5A:
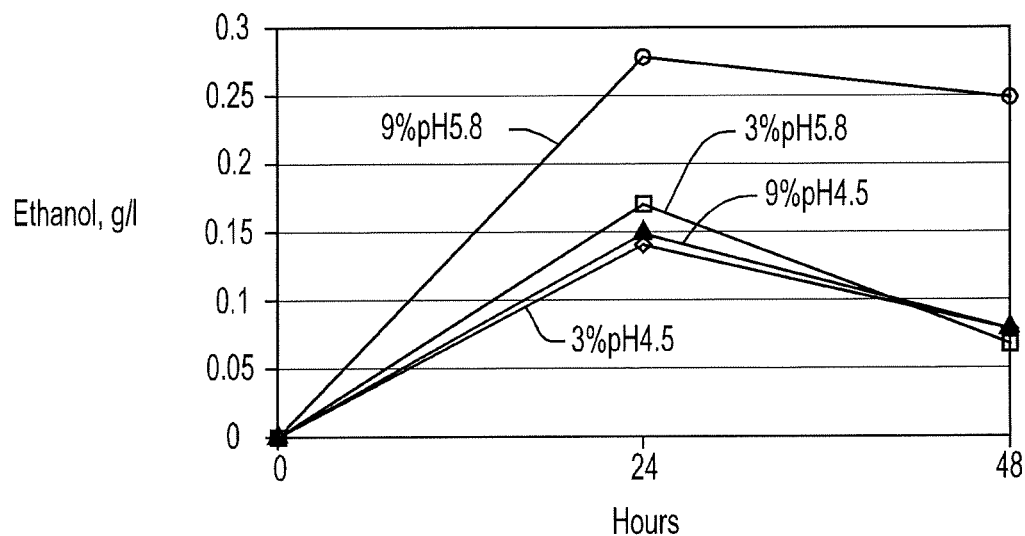
FIG. 5. Ethanol production by the *H. polymorpha* recombinant strain 495 2Eth-leu1-1/pOR2 in the minimal YNB medium with 3% or 9% birchwood xylan with different pH medium (A) and aeration conditions (B). 48° C.

The effect of pH of the medium on ethanol production during the xylan fermentation was investigated. Fermentation was carried out using media with pH 4.5 and 5.8. A 1M solution of potassium phosphate buffer was used to adjust medium pH with final concentration 0.1M in the medium. The best ethanol production was achieved in the medium with pH 5.8 (FIG. 5A).

Figure 5B:
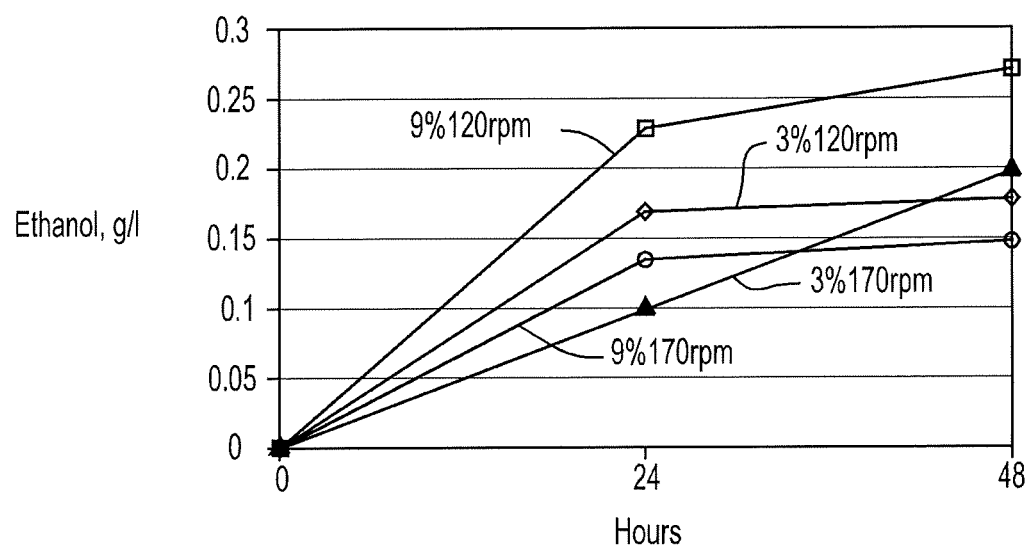

Effect of aeration on the fermentation efficiency was studied. Rotation rates from 120 to 180 rpm were tested. The highest ethanol production was in the case of 120 rpm (FIG. 5B). The higher xylan concentration (9%) resulted in better ethanol production (FIG. 5).

Southern Blot Hybridization

The labeling of probe DNA and hybridization was performed using the non-radioactive Amersham ECL Direct Nucleic Acid Labeling and Detection System (GE Healthcare, USA) according to the manufacturer's manual. For quantitative Southern dot-blot, preparations of serial dilutions of yeast genomic DNAs were denatured in 0.4 M NaOH, spotted onto dry nylon membrane (Hybond N+, Amersham Pharmacia Biotech) and labeled with appropriate DNA fragments, followed by visualization with the Amersham ECL detection kit as above. HpGAPpr was used as a probe.

Gel Electrophoresis

SDS-PAGE was performed by method of Laemmli [19]. Concentrated proteins from cell-free extract were visualized by Silver staining and staining with Coomassie brilliant blue. The running and stacking gel concentration was 12% and 5% of poly acryl amid respectively. 20 µl of Laemmli solution added to 20 µl of sample and 35 µl of mixture was injected to the running gel [31].

Results

Expression of SWA2 and GAM1 Genes of *Scw. occidentalis* in *H. polymorpha*

Figure 6:
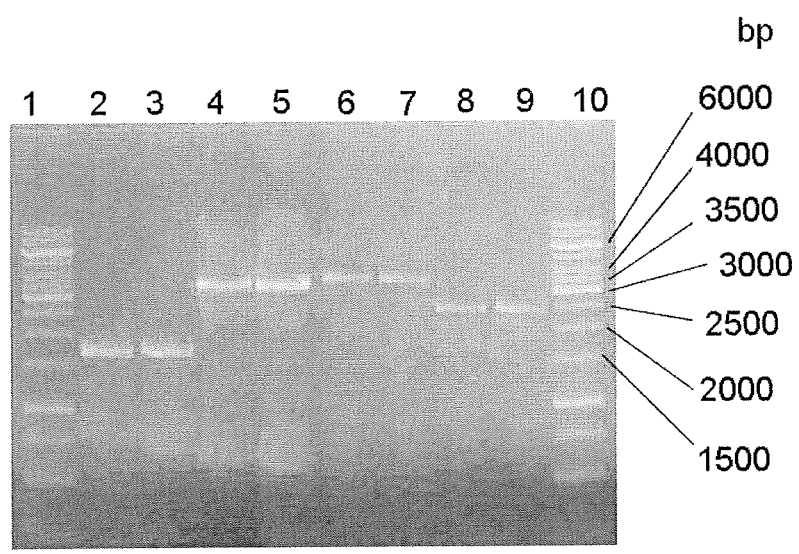
FIG. 6. Demonstration of genes GAM1, SWA2, XYN2, and xlnD under the HpGAP promoter in genomic DNA of *H. polymorpha* transformants by means of PCR. Lane ## 2, 3: the pair of primers K43, Ko51 was used for analysis of the transformants obtained by transformation with the plasmid pOR2 to show the artificial construct: *T. reesei* XYN2 ORF fused with the HpGAP promoter and HpAOX terminator. Lane ##4, 5: the pair of primers K43, Ko47 was used for analysis of the transformants obtained by plasmid pOR2 to show the construct: *A. niger* xlnD fused with the HpGAP promoter. Lane ##6, 7: the pair of primers K43, Ko49 was used for analysis the transformant obtained by plasmids pOR1 and pOR11 to show the construct: GAM1 of *Scw. occidentalis* fused with the HpGAP1 promoter. Lane ##8, 9: the pair of primers K43, Ko50 was used for analysis of the transformants obtained by plasmids pOR1 and pOR11 to show the construct: ORF of *Scw. occidentalis* SWA2 fused with the HpGAP1 promoter and HpAOX termonator. Lane ##1, 10: DNA markers.
Figure 7A:
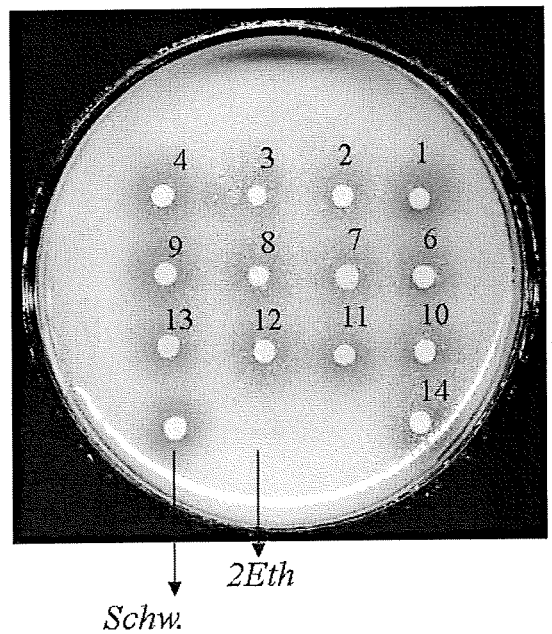
FIG. 7. Formation of the clear halos by the *H. polymorpha* recombinants that express the *Scw. occidentalis* SWA2 and GAM1 genes driven by the HpGAP1 promoter. The control *Scw. occidentalis* strain does not produce a halo on the medium supplemented with glucose (B) because of repression of native promoters of SWA2 and GAM1 genes. The second control 2Eth⁻ leu1-1 strain cannot grow on the medium with starch as sole carbon source (A).
Figure 7B:
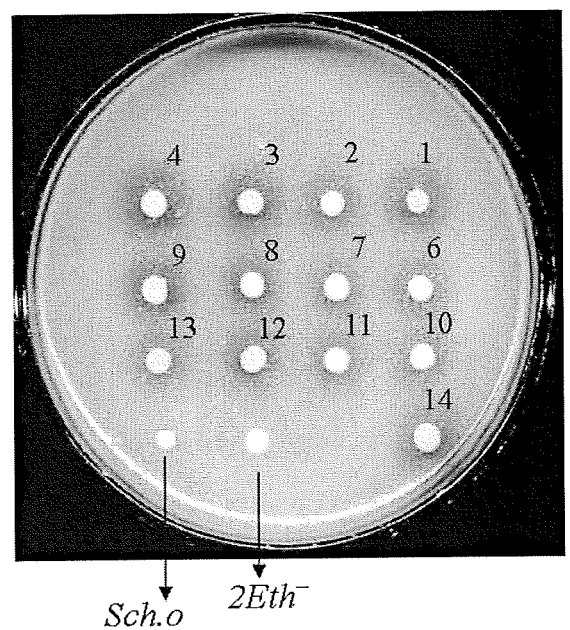
Figure 8:
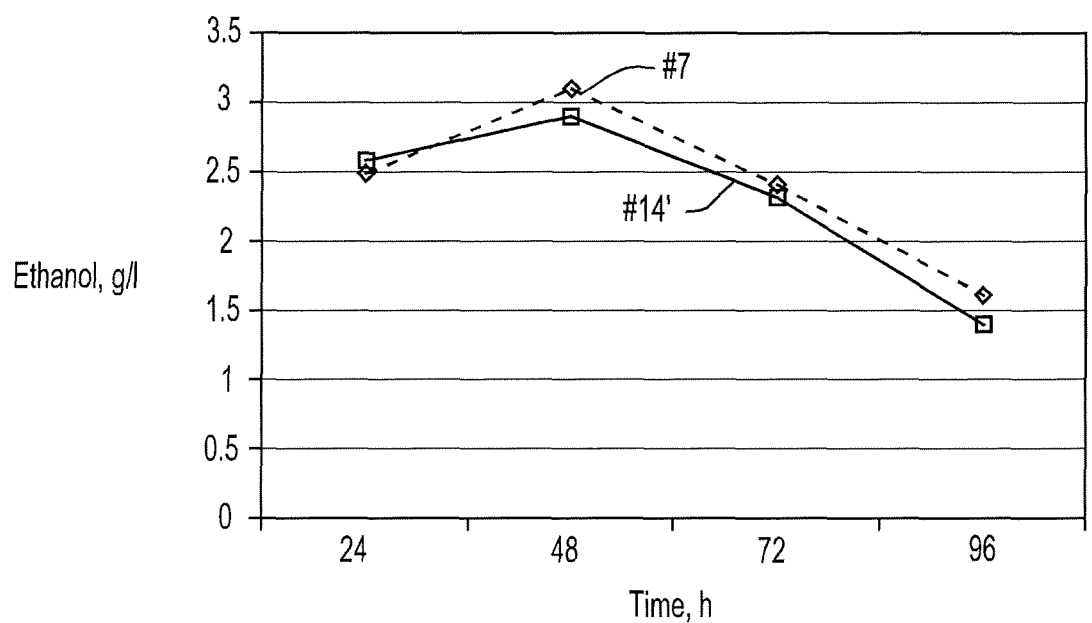
FIG. 8. Ethanol production by the *H. polymorpha* recombinant strains 2Eth⁻ leu1-1/pOR1 ##7 and 14' in the minimal YNB medium with 2% of the soluble starch, 48° C., 135 rpm.
Figure 9A:
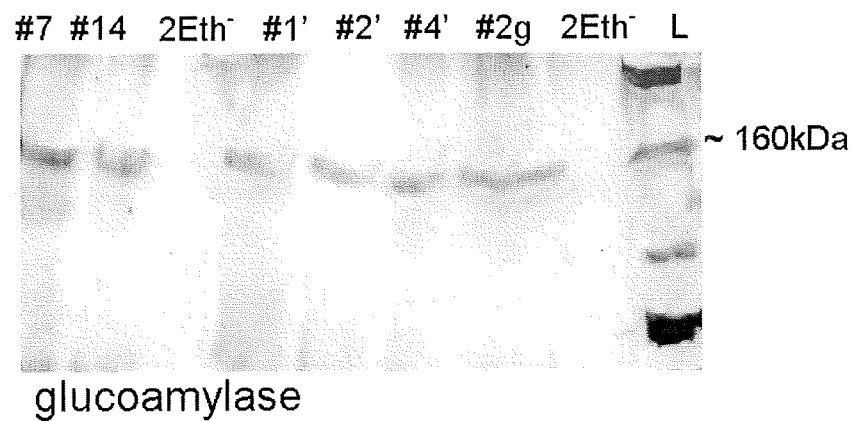
FIG. 9. SDS-PAGE analysis of cultural media of the recombinant strains #7, 14 (495 2Eth⁻ leu1-1/pOR1), 1', 2' 4', 2 g (495 2Eth⁻ leu1-1/pOR11) and recipient strain 495 2Eth⁻ leu1-1. Electrophoresis was carried out using 8% separation gel, protein bands were visualized by Coomasie and Silver staining. A, visualization of glucoamylase; B, visualization of α-amylase; the diffuse bands of α-amylase presumably are because of differing degrees of glycosylation. L, protein molecular weight marker.
Figure 9B:
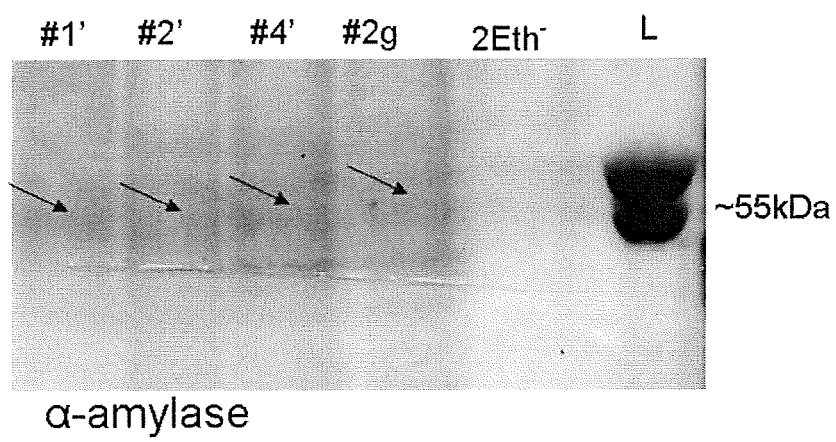

The *H. polymorpha* strain 495 2Eth⁻ leu1-1 was used as a recipient for transformation by the Sph I linearized plasmid pOR1 (scheme of the plasmid is shown in FIG. 1). After transformation cells were plated on a minimal medium supplemented with 2% glucose and 1% soluble starch. Among ~140 transformants the 14 that formed the largest amylolytic clear halos were picked out. Presence of SWA2 and GAM1 genes under the HpGAPpr in these transformants was shown by PCR using corresponding primers (FIG. 6). The transformants were able to grow on soluble starch and ferment the substrate to ethanol at 37 and 48° C. Efficient secretion of amylases with the integrants was shown by formation of clear halos around the colonies (FIGS. 7 A & B). The best selected integrant (2Eth⁻ leu1-1/pOR1 #7) produced over 3 g/L of ethanol after 48 hours of fermentation in a minimal medium with 3% soluble starch at pH 5.5, 48° C. (FIG. 8). To obtain *H. polymorpha* strains with improved amylolytic activity we tried to increase the SWA2 and GAM1 copy numbers. With this aim the plasmid pOR11 (FIG. 3) carrying the dominant marker (APH gene that confers resistance to G418) and genes SWA2 and GAM1 was used. The *H. polymorpha* strain 495 2Eth⁻ leu1-1 was used as a recipient for transformation by the Sph I linearized plasmid pOR11. After transformation, cells were plated on a YPD medium with 0.2 g/l G418. 5 stable transformants were found and picked out among ~80 resulting G418-resistant colonies. Presence of the SWA2 and GAM1 genes under the HpGAPpr in these transformants was shown by PCR using corresponding primers (FIG. 6). Production of recombinant enzymes (α- and glucoamylase) by these strains was demonstrated by the SDS-PAGE (FIGS. 9 A & B).

Figure 10:
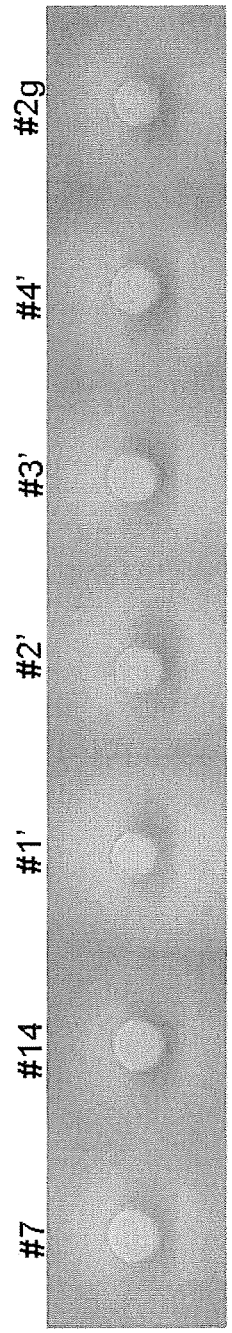
FIG. 10. Formation of clear halos by the *H. polymorpha* recombinants ##7, 14 (495 2Eth⁻ leu1-1/pOR1) and multicopy integrants ##1', 2', 3', 4' and 2 g (495 2Eth⁻1/pOR11).
Figure 11:
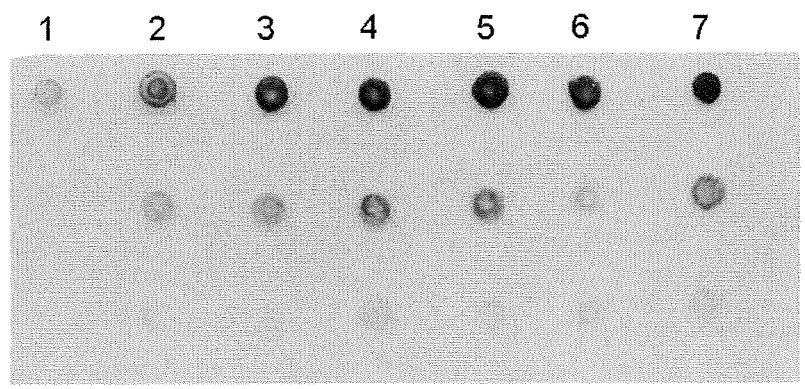
FIG. 11. Results of dot-blot Southern hybridization that illustrate a copy number of genes encoding amylolytic enzymes in *H. polymorpha* transformants. The promoter of HpGAP was used as a probe. Strains: 1-wt (1 copy standard); 2, 3-##7, 14 (about 3-4 copies); 4, 5, 7-#141', 2', 4', respectively (about 6-8 copies); 6-#3' (~3 copies).

Isolates following transformation with the plasmid pOR11 formed larger amylolytic clear halos in comparison with the best transformants isolated earlier from the pOR1 plasmid (FIG. 10). Southern hybridization demonstrated presence of approx. 6-8 copies of the SWA2 and GAM1 genes in the isolated transformants (FIG. 11).

Figure 12A:
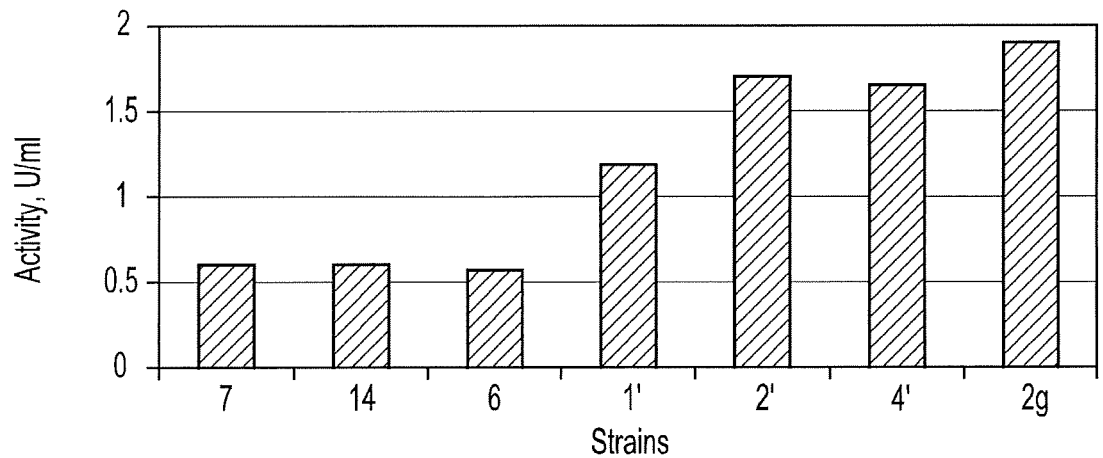
FIG. 12. Specific activity of α-amylase (A) and glucoamylase (B) in cultural media of the recombinant yeast strains # #7, 14, 6 (495 2Eth⁻ leu1-1/pOR1) containing 3-4 copies of amylase genes and ##1', 2' 4', 2 g (495 2Eth⁻ leu1-1/pOR11) containing 6-8 copies of the genes.
Figure 12B:
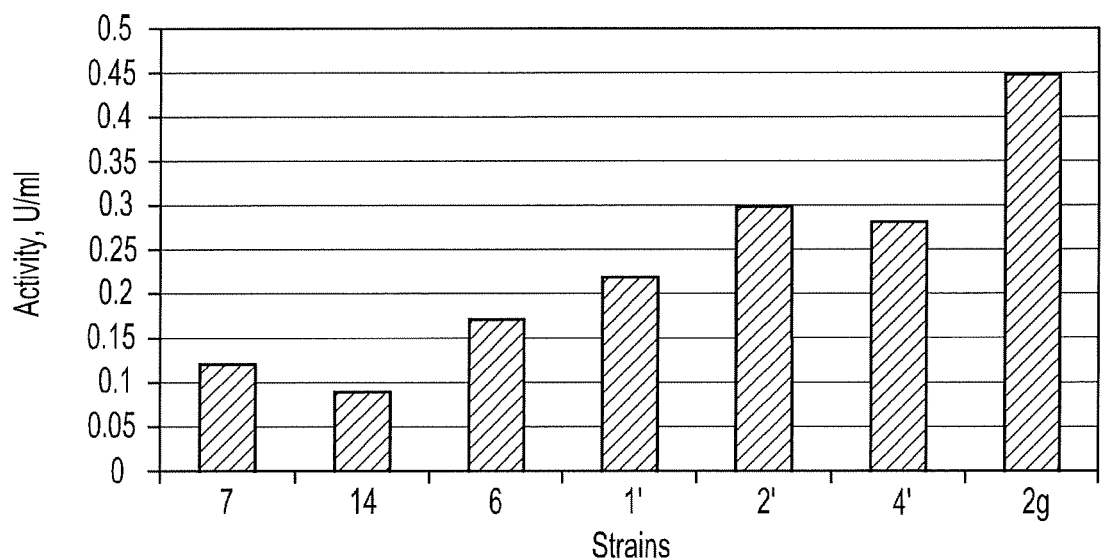

The transformants 495 2Eth⁻ leu1-1/pOR11 showed higher activity of both α- and glucoamylase when compared with strains which contain only 3-4 copies of the amylase genes (FIGS. 12 A & B).

Figure 13:
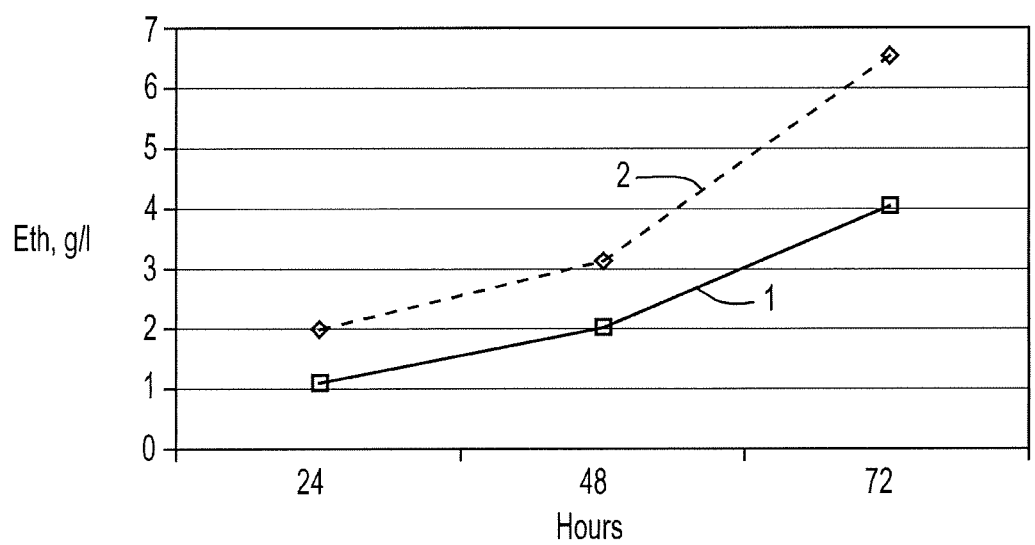
FIG. 13. Ethanol production by the *H. polymorpha* recombinants 2Eth⁻ leu1-1/pOR1 (#1: an average of ethanol production of the strains ##7 and 14) and 2Eth⁻ leu1-1/pOR11 (#2: an average of ethanol production of the strains ##1', 2', 4', 2 g). The strains were cultivated in the minimal YNB medium with 3% of soluble starch at pH 5.5, 48° C., 135 rpm.

Effectiveness of alcoholic starch fermentation of isolated transformants was studied. These transformants showed elevated ethanol production (6.5 g/L after 72 hr of cultivation) as compared with transformants isolated earlier by the pOR1 transformation. The fermentation was carried out in the minimal YNB medium with 3% of soluble starch at pH 5.5, 48° C., 135 rpm (FIG. 13).

Figure 14:
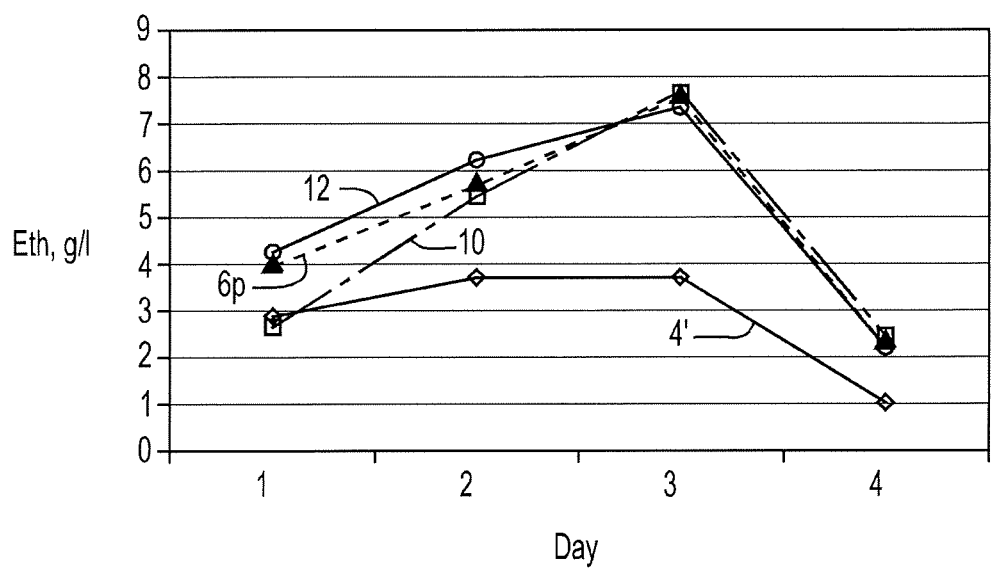
FIG. 14. Ethanol production by the *H. polymorpha* strains overexpressing genes of amylolytic enzymes and PDC1 gene in the minimal medium with 3% soluble starch; 48° C., 135 rpm. 4', the transformant 495 2Eth⁻ leu1-1/pOR11 (recipient strain, control); 6p, 10, 12, the transformants 4'/ploxZeoloxPDC1Hp.

Isolating the Strains of *H. polymorpha* with Improved Properties of Starch Fermentation The plasmid ploxZeoloxPDC1Hp constructed earlier in our laboratory [13], was used for obtaining of *H. polymorphs* strains with improved amylolytic properties. Following overexpression of the pyruvate decarboxylase gene (PDC1), these strains were characterized with improved ethanol production when compared to the control strain 495 2Eth⁻[13]. The plasmid ploxZeoloxPDC1Hp that contains the PDC1 gene driven with the HpGAPpr was linearized by BamHI and used for transformation of the strain #4', isolated earlier (495 2Eth⁻/pOR1). Zeocine resistant transformants were selected on a YPD medium supplemented with 150 µg/ml of zeocine. Some of the stable integrants were selected for further study. Effectiveness of the alcoholic fermentation of these recombinants was studied. All of the transformants showed higher levels of the ethanol production (7-8 g/L) compared with the 4' strain (up to 4 g/L; FIG. 14).

Figure 15:
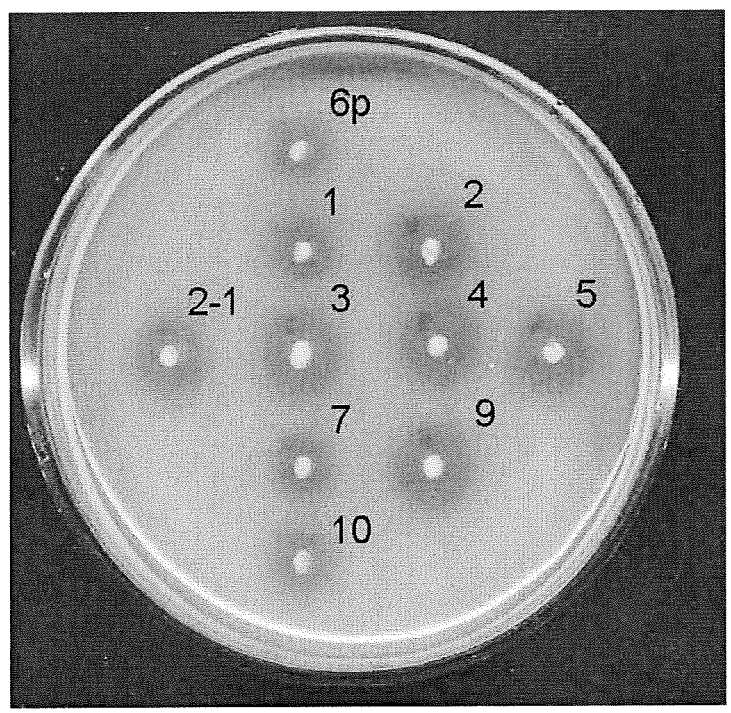
FIG. 15. Formation of clear halos by the *H. polymorpha* recombinant #6p (4'/ploxZeoloxPDC1Hp) and its derivatives: integrants ##1, 2, 2-1, 3, 4, 5, 7, 9, 10 (6p/pOR1).
Figure 16:
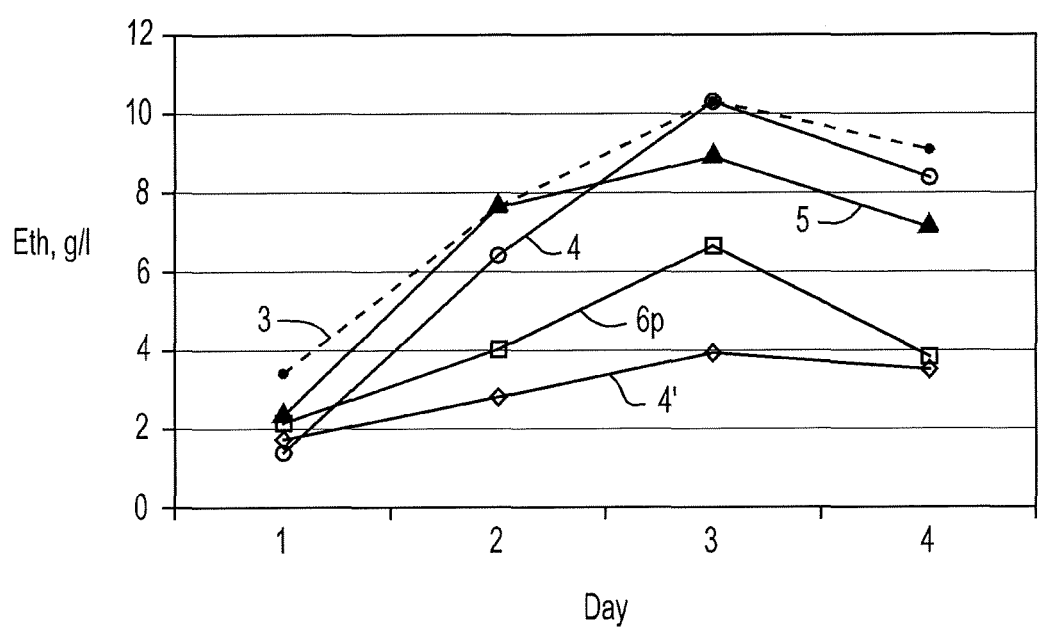
FIG. 16. Ethanol production by the *H. polymorpha* strains overexpressing amylolytic enzymes and Pdc1p in the minimal medium with 3% soluble starch at 47° C. with restricted aeration. 4', the transformant 495 2Eth⁻ leu1-1/pOR11; 6p, the transformant 4'/pZeoloxPDC1Hp; 3, 4, 5, the transformants 6p/pOR1.

The strain #6 (the transformant 4'/ploxZeoloxPDC1Hp, which showed the highest level of the ethanol production) was used as a recipient for transformation with the plasmid pOR1 linearized with Sph I. The Leu⁺ transformants were selected on a minimal medium without leucine and stabilized. Stable transformants were plated on a minimal medium supplemented with 2% soluble starch. Some of the integrants, which formed larger clear halos in compare with the strain #6, were selected for further study (FIG. 15). Effectiveness of alcoholic fermentation of these recombinants was studied. All of the transformants showed higher levels of the ethanol production (9-10 g/L) when compared with the strain #6 (FIG. 16).

Expression of *T. reesei* XYN2 and *A. niger* XLND Genes in *H. polymorpha*

The plasmid pOR2 containing the *T. reesei* XYN2 and *A. niger* xlnD genes driven with the HpGAPpr (FIG. 3) was linearized by SphI and used for transformation of the *H. polymorpha* strain 495 2Eth⁻ leu1-1. Leu⁺ transformants were stabilized. The presence of the XYN2 and xlnD genes under the HpGAPpr in transformants was tested by PCR using corresponding primers (FIG. 6).

Figure 18A:
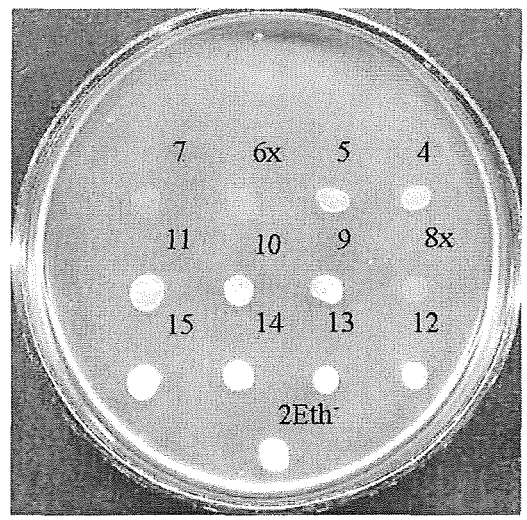
FIG. 18. Formation of yellow (A) or clear (B) halos by the *H. polymorpha* recombinants expressing the *A. niger* xlnD and *T. reseei* XYN2 genes.
Figure 18B:
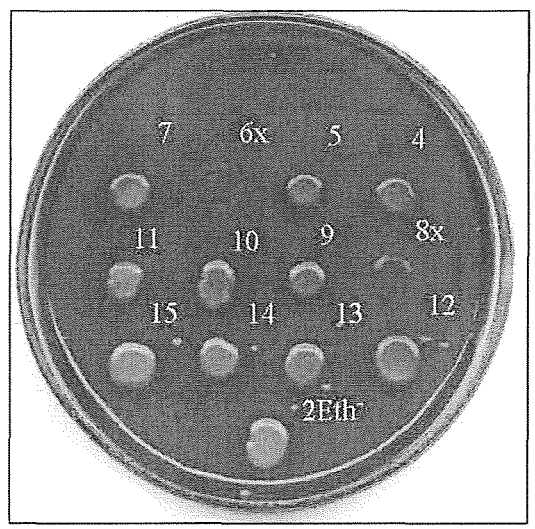
Figure 19A:
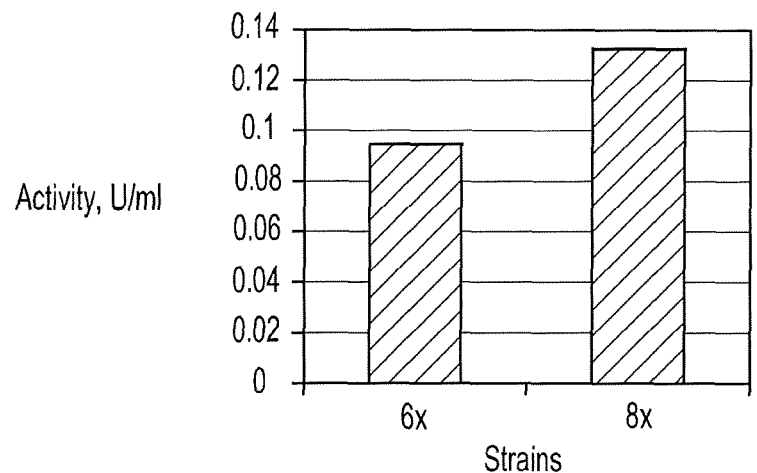
FIG. 19. Specific activity of the endoxylanase (A) and β-xylosidase (B) in culture medium of the *H. polymorpha* recombinant strains 495 2Eth⁻/pOR2 ##6× and 8×.
Figure 19B:
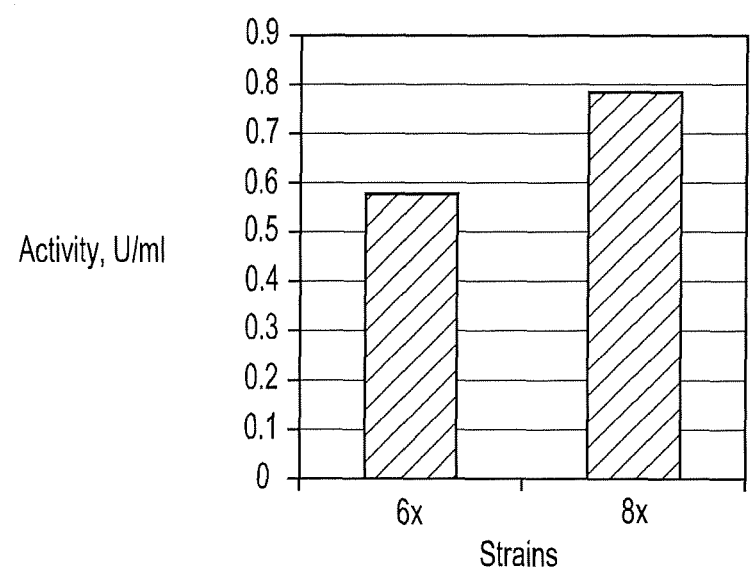

Transformants were able to grow on xylan as the sole carbon source (FIGS. 17, A, B1 and B2). Efficient secretion of the endoxylanase and β-xylosidase with the integrants was shown by formation of clear or yellow halos on media containing 0.2% RBB-xylan or 1 mM PNPX, respectively (FIGS. 18 A and B). The activity of both enzymes was measured (FIGS. 19 A and B). The transformants were able to ferment birchwood xylan to ethanol with low efficiency (approx. 0.35 g/L) at both 37 and 48° C.

Co-Expression of *T. reesei* XYN2, *A. niger* XLND, with *Scw. occidentalis* SWA2 and GAM1 Genes of in *H. polymorpha*

In a first case, the transformants 495 2Eth⁻ leu1-1/pOR11 containing both the α-amylase and glucoamylase genes from *Scw. occidentalis* integrated into the chromosome of *H. polymorpha* is used the host strain. The plasmid pOR2 containing the *T. reesei* XYN2 and *A. niger* xlnD genes driven with the HpGAPpr is linearized by SphI and used for transformation of the *H. polymorpha* strain 495 2Eth⁻ leu1-1/pOR11. The transformants are stabilized as before. The presence of the XYN2 and xlnD genes is tested by PCR using corresponding primers Transformants will be able to grow with soluble starch and/or soluble xylan as the sole carbon source. Efficient secretion of all four enzymes will be demonstrated essentially as described above. The transformants will be able ferment a mixed media containing both soluble starch and birchwood xylan into ethanol at both 37 and 48°.

In a second case, the transformant described above, having both the α-amylase and glucoamylase genes already transformed in to the strain, 4'/ploxZeoloxPDC1Hp, which over expresses the PDC gene is used as the host strain. Again, the plasmid pOR2 containing the *T. reesei* XYN2 and *A. niger* xlnD genes driven with the HpGAPpr is linearized by SphI and used for transformation of the *H. polymorpha* host strain. The transformants are stabilized as before. The presence of the XYN2 and xlnD genes is tested by PCR using corresponding primers Transformants will be able to grow with soluble starch and/or soluble xylan as the sole carbon source. Efficient secretion of all four enzymes will be demonstrated essentially as described above. The transformants will be able ferment a mixed media containing both soluble starch and birchwood xylan into ethanol at both 37 and 48° at a level higher than the transformants made in the first case due to the complimentary over expression of the PDC enzyme in the host cell.

Discussion

Fuel ethanol production from renewable plant material has a great economic and ecological significance. One of the byproducts from the corn wet milling industry that is readily available in large quantities is the corn fiber hull fraction. This fraction is mixed and dried with other processing byproducts and stillage fraction from ethanol fermentation to produce corn gluten feed. Corn fiber hulls consist of 35% hemicellulose, 18% cellulose and 20% starch (protein, fiber oil and lignin are also present in this material) [7]. Xylan is the major component of hemicellulose. Industrial steps which include enzymatic hydrolysis of xylan and starch are very expensive. Therefore the direct microbial conversion of these polymers to ethanol is of great economical significance. For this reason developing microorganisms capable of simultaneous hydrolysis of starch and xylan and fermentation of the released sugars to ethanol at elevated temperatures has a great importance for fuel ethanol production from corn. Glucose and xylose are the main sugars released after starch and xylan hydrolysis, respectively. The yeast *H. polymorpha* ferments glucose and xylose to ethanol at high temperatures. However, *H. polymorpha* cannot utilize starchy materials and xylan and grow on them as on sole carbon sources.

We cloned two genes from the yeast *Scw. occidentalis* SWA2 and GAM1 which encode α-amylase and glucoamylase, respectively. Both of these enzymes are needed for starch hydrolysis. SWA2 and GAM1 genes were successfully expressed in *H. polymorpha*. Isolated recombinant strains are capable to grow on starch as sole carbon source. They are also able to ferment soluble starch to ethanol at 48° C. We showed that increasing gene copy numbers improves the capability of recombinant strains to starch hydrolysis and ethanol production.

Genes of *T. reesei* XYN2 and *A. niger* xlnD encoding endoxylanase and β-xylosidase, respectively, were cloned and expressed in *H. polymorpha*. At least two these enzymes are necessary for xylan hydrolysis. Isolated integrants were capable of growth on xylan as sole carbon source and fermentation it to ethanol at both 37 and 48° C. The low effectiveness of conversion of xylan to ethanol by isolated strains is most likely due to the initial low capability of *H. polymorpha* strains for xylose alcoholic fermentation. Further improvement in xylan fermentation by the strains constructed will require improved ethanolic fermentation of xylose as a prerequisite. These strains can then be used as recipients for construction of effective xylanolytic recombinants.

REFERENCES

1. Bailey, M. J., P. Biely, and K. Poutanen. 1992. Interlaboratory testing of methods for assay of xylanase activity. J. Biotechnol. 23: 257-270.
2. Banat, I. M., P. Nigam, D. Singh, P. Marchant, and A. P. McHale. 1998. Ethanol production at elevated temperatures and alcohol concentrations. Part I: yeasts in general. World J Microbiol Biotechnol. 14: 809-821.
3. Dmytruk, O. V., A. Y. Voronovsky, C. A. Abbas, K. V. Dmytruk, O. P. Ishchuk, and A. A. Sibirny. 2008. Overexpression of bacterial xylose isomerase and yeast host xylulokinase improves xylose alcoholic fermentation in the thermotolerant yeast *Hansenula polymorpha*. FEMS Yeast Res. 8: 165-173.
4. Eksteen, J. M., P. van Rensburg, R. R. Cordero Otero, and I. S. Pretorius. 2003. Starch fermentation by recombinant *Saccharomyces cerevisiae* strains expressing the α-amylase and glucoamylase genes from *Lipomyces kononenkoae* and *Saccharomycopsis fibuligera*. Biotechnol. Bioengineer. 84: 639-646.
5. Faber, K N, P. Haima, W. Harder, M. Veenhuis, and G. Ab. 1994. Highly-efficient electrotransformation of the yeast *Hansenula polymorpha*. Curr. Genet. 25: 305-310.
6. Fujita, Y., and J. Ito. 2004. Synergistic saccharification, and direct fermentation to ethanol, of amorphous cellulose by use of an engineered yeast strain codisplaying three types of cellulolytic enzyme. Appl. Environ. Microbiol. 70: 1207-1212.
7. Gaspar, M., G. Kalman, and K. Reczey. 2007. Corn fiber as a raw material for hemicellulose and ethanol production. Process Biochem. 42: 1135-1139.
8. Gellissen, G., G. Kunze, C. Gaillardin, J. M. Cregg, E. Berardi, M. Veenhuis, and I. van der Klei. 2005. New yeast expression platforms based on methylotrophic *Hansenula polymorpha* and *Pichia pastoris* and on dimorphic *Arxula adeninivorans* and *Yarrowia lipolytica* a comparison. FEMS Yeast Res. 5:1079-1096.
9. Gonchar, M. V. 1998. Sensitive method for quantitative determination of hydrogen peroxide and oxidase substrates in biological samples. Ukr. Biokhim. Zh. 70: 157-163.
10. Gonchar, M. V., M. M. Maidan and A. A. Sibirny. 2001. A new oxidase-peroxidase kit for ethanol assays in alcoholic beverages. Food Technol. Biotechnol. 39: 37-42.
11. den Haan R., and W. H. van Zyl. 2001. Differential expression of the *Trichoderma reesei* β-xylanase II (xyn2) gene in the xylose-fermenting yeast *Pichia stipitis*. Appl Microbiol Biotechnol. 57: 521-527.
12. Haki, G. D., and S. K. Rakshit. 2003. Developments in industrially important thermostable enzymes: a review. Bioresource Technology. 89: 17-34.
13. Ishchuk, O. P., A. Y. Voronovsky, O. V. Stasyk, G. Z. Gayda, M. V. Gonchar, C. A. Abbas, and A. A. Sibirny. 2008. Improvement of xylose high-temperature fermentation in *Hansenula polymorpha* due to overexpression of the PDC1 gene coding for pyruvate decarboxylase. FEMS Yeast Res. In press.
14. Jeffries, T. W., and Y. S. Jin. 2000. Ethanol and thermotolerance in the bioconversion of xylose by yeasts. Adv. Appl. Microbiol. 47: 221-268.
15. Kadam, K. L., and S. L. Schmidt. 1997. Evaluation of *Candida acidothermophilum* in ethanol production from lignocellulosic biomass. Appl. Microbiol. Biotechnol. 48:709-713.
16. Kang, N. Y., J. N. Park, J. E. Chin, H. B. Lee, S. Y. Im, and S. Bai. 2003. Construction of an amylolytic industrial strain of *Saccharomyces cerevisiae* containing the *Schwanniomyces occidentalis* α-amylase gene. Biotechnol. Lett. 25: 1847-1851.
17. Kılıç, D., and B. Özbek. 2004. α-Amylase inactivation by temperature during starch hydrolysis. Process Biochem. 39: 1137-1144.
18. Kulkarni, N., A. Shendye, and M. Rao. 1999. Molecular and biotechnological aspects of xylanases. FEMS Microbiol. Rev. 23: 411-456.
19. La Grange, D. C., I. S. Pretorius, M. Claeyssens, and W. H. van Zyl. 2001. Degradation of xylan to D-xylose by recombinant *Saccharomyces cerevisiae* coexpressing the *Aspergillus niger* β-xylosidase (xlnD) and the *Trichoderma reesei* xylanase II (xyn2) genes. Appl. Environ. Microbiol. 67: 5512-5519.
20. La Grange, D. C., I. S. Pretorius, and W. H. van Zyl. 1996. Expression of a *Trichoderma reesei* β-xylanase gene (XYN2) in *Saccharomyces cerevisiae*. Appl. Environ. Microbiol. 62: 1036-1044.
21. Laemmli, U. K. 1970. Cleavage of structural proteins during the assembly of the head of bacteriophage T4. Nature. 227: 680-685.
22. Liu, Z., G. Zhang, and S. Liu. 2004. Constructing an amylolytic brewing yeast *Saccharomyces pastorianus* suitable for accelerated brewing. J. Biosci. Bioeng. 98: 414-419.
23. Marin, D., A. Jimenez, and M. Fernandez Lobato. 2001. Construction of an efficient amylolytic industrial yeast strain containing DNA exclusively derived from yeast. FEMS Microbiol. Lett. 201: 249-253.
24. Mosier, N., and C. Wyman. 2005. Features of promising technologies for pretreatment of lignocellulosic biomass. Bioresour. Technol. 96: 673-686.
25. Piontek, M., J. Hagedorn, C. P. Hollenberg, G. Gellissen, and A. W. M. Strasser. 1998. Two novel gene expression systems based on the yeasts *Schwanniomyces occidentalis* and *Pichia stipitis*. Appl. Microbiol. Biotechnol. 50: 331-338.
26. Ryabova, O. B., O. M. Chmil and A. A. Sibirny. 2003. Xylose and cellobiose fermentation to ethanol by the thermotolerant methylotrophic yeast *Hansenula polymorpha*. FEMS Yeast Res. 4: 157-164.
27. Sambrook, J., E. F. Fritsh, and T. Maniatis. Molecular Cloning: A Laboratory Manual. Cold Spring Harbor Laboratory, Cold Spring Harbor, N.Y. 1989.
28. Shigechi, H., Y. Fujita, J. Koh, M. Uedac, H. Fukuda, and A. Kondo. 2004. Energy-saving direct ethanol production from low-temperature-cooked corn starch using a cell-surface engineered yeast strain co-displaying glucoamylase and α-amylase. Biochem. Eng. J. 18: 149-153.
29. Shigechi, H., J. Koh, Y. Fujita, T. Matsumoto, Y. Bito, M. Ueda, E. Satoh, H. Fukuda, and A. Kondo. 2004. Direct production of ethanol from raw corn starch via fermentation by use of a novel surface-engineered yeast strain codisplaying glucoamylase and α-amylase. Appl. Environ. Microbiol. 70: 5037-5040.
30. Sohn, J. H., E. S. Choi, H. A. Kang, J. S. Rhee, M. O. Agaphonov, M. D. Ter-Avanesyan, and S. K. Rhee. 1999. A dominant selection system designed for copynumber-controlled gene integration in *Hansenula polymorpha* DL-1. Appl Microbiol Biotechnol. 51: 800-807.
31. Torronen, A., L. R. Mach, R. Massner, R. Gonzales, N. Kalkkinen, A. Harkki, and C. P. Kubicek. 1992. The two major xylanases from *Trichoderma reesei*: characterization of both enzymes and genes. Biothechnology. 10: 1461-1465.
32. Ulgen, K. O., and B. Saygili. 2002. Bioconversion of starch into ethanol by a recombinant *Saccharomyces cerevisiae* strain YPG-AB. Process Biochem. 37: 1157-1168.
33. de Vries, R. P. and J. Visser. 2001. *Aspergillus* enzymes involved in degradation of plant cell wall polysaccharides. Microbiol. Mol. Biol. Rev. 65: 497-522.
34. Wang, T. T., L. L. Lin, and W. H. Hsu. 1989. Cloning and expression of a *Schwanniomyces occidentalis* α-amylase gene in *Saccharomyces cerevisiae*. Appl. Environment. Microbiol. 55: 3167-3172.
35. Zaldivar, J., J. Nielsen, and L. Olsson. 2001. Fuel ethanol production from lignocellulose: a challenge for metabolic engineering and process integration. Appl Microbiol Biotechnol. 56: 17-34.

The invention claimed is:

1. A *H. polymorpha* strain comprising at least one gene encoding an α-amylase enzyme according to SEQ ID NO: 2 and at least one gene encoding a glucoamylase enzyme according to SEQ ID NO: 4, the genes being operably linked to a HpGAP promoter obtained from *H. polymorpha* that expresses said genes in the *H. polymorpha* strain, and further including a gene encoding a pyruvate decarboxylase enzyme from *H. polymorpha* operably linked to a HpGAP promoter that expresses said pyruvate decarboxylase in the *H. polymorpha* strain and wherein said α-amylase and said glucoamylase enzymes are exported from the *H. polymorpha* strain into a media in sufficient amounts to permit growth of the *H. polymorpha* strain in a medium solely containing soluble starch as a carbon source at a temperature with-of 48° C.

2. The *H. polymorpha* strain of claim 1 wherein the gene encoding at least one of the α-amylase and glucoamylase is integrated into the *H. polymorpha* chromosome.

3. The *H. polymorpha* strain of claim 1 wherein each of the genes encoding the α-amylase and glucoamylase are integrated into the *H. polymorpha* chromosome.

4. The *H. polymorpha* strain of claim 1 wherein at least one gene encoding the α-amylase enzyme or the glucoamylase enzyme further includes a terminator operably linked to said gene to terminate transcription of the expressed gene.

5. A process for making ethanol comprising growing the *H. polymorpha* strain of claim 1 in a media comprising soluble starch under conditions that cause the *H. polymorpha* to make ethanol.

6. The *H. polymorpha* strain of claim 1 further comprising at least one gene encoding an endoxylanase enzyme according to SEQ ID NO: 8 and at least one gene encoding a β-xylosidase enzyme according to SEQ ID NO: 6, each gene being operably linked to at least one promoter that expresses said genes in the *H. polymorpha* strain wherein each of said endoxylanse and β-xylosidase enzymes are exported from the *H. polymorpha* strain into a media in sufficient amounts to permit growth of the *H. polymorpha* strain in a medium containing solely or in sole combination, a soluble starch and a soluble xylan as the carbon source.

7. A process for making ethanol comprising growing the *H. polymorpha* strain of claim 6 in a media comprising soluble starch and a xylan under conditions that cause the *H. polymorpha* to make ethanol.

* * * * *

SEQUENCE LISTING

<160> NUMBER OF SEQ ID NOS: 12

<210> SEQ ID NO 1
<211> LENGTH: 1539
<212> TYPE: DNA
<213> ORGANISM: Schwanniomyces Occidentalis

<400> SEQUENCE: 1

```
atgagatttt caactgaagg atttacaagt aaagttgttg cagcaatttt agcattctca      60
agattggtat ctgctcaacc gattattttt gacatgagag atgttagctc gtcagctgat     120
aaatggaaag accaatcgat ttatcaaatc gttactgata ggtttgccag atctgatggc     180
tcgaccacag ctgactgttt agtgagtgat cgcaagtact gtggtggatc ttataaaggg     240
attatcgaca agttggatta tattcaaggt atgggtttca ctgcgatctg gatctcccca     300
gttgttgagc aaattcctga caatactgct tatggttatg cttaccatgg ttattggatg     360
aaaaatattg atgaattgaa cactaatttt ggtaccgctg atgaattgaa acaattagct     420
agcgaattgc attccagaag catgttattg atggtcgacg ttgtttacaa ccattatgct     480
tggaacggag atggttcaag cgtagattat tctagtttca ctccattcaa tcaacaatct     540
tacttccacg attattgttt gattacaaat tataatgatc aaaccaatgt tgaagattgt     600
tgggaaggtg atactgaagt ctcccttcca gatttaagta ccgaggataa tgaagttata     660
ggagtatttc aaacttgggt gtcagatttt gttcaaaact attcaatcga tggtttaaga     720
attgatagtg caaagcacgt agataccgct tcattaacga gtttgagga cgcttctggt     780 gtttataact taggtgaagt ttatcaagga gatccaactt atacttgtcc atatcagaat     840
tatatgaaag gagttaccaa ctatccatta tactatccag tatatagatt cttcagtgat     900
acttcggcga cttccagtga gttaacttca atgatctcca cgttacagtc atcttgttcg     960
gacgtctctt tgttgggaaa ctttattgaa aaccatgacc aagttagatt tccatcagtt    1020
acctcagaca catccttgat taagaatgac atggcttta taattttggg tgatggtatc    1080
ccaattattt attatgccca agaacaaggt ctcaatggtg gttccgatcc tgccaataga    1140
gaagctttat ggttaagtgg atataatacc gattcagaat actacgagct aatcagtaaa    1200
ctaaatcaaa taagaaatca agctattaag aaggattctg cctattcaac ttacaaatcc    1260
tcagttgttt cttcttcaga ccactatata gccactagga agggtagcga tgctaatcaa    1320
ttgatttcca tttttaataa tttaggttca aacgggtcac aggatattac tgtcagcaac    1380
accggctatt ctagtggtga taaagttatc gatattattt cttgcaattc cgttttagct    1440
ggtgactccg gaagcttatc tgtatcaatt tctggtggaa tgccacaagt ttacgctccg    1500
tcctctgttc tttcgggatc tggcatctgc aatcaatag                           1539
```

<210> SEQ ID NO 2
<211> LENGTH: 512
<212> TYPE: PRT
<213> ORGANISM: Schwanniomyces Occidentalis

```
<400> SEQUENCE: 2

Met Arg Phe Ser Thr Glu Gly Phe Thr Ser Lys Val Val Ala Ala Ile
 1               5                  10                  15

Leu Ala Phe Ser Arg Leu Val Ser Ala Gln Pro Ile Ile Phe Asp Met
             20                  25                  30

Arg Asp Val Ser Ser Ser Ala Asp Lys Trp Lys Asp Gln Ser Ile Tyr
         35                  40                  45

Gln Ile Val Thr Asp Arg Phe Ala Arg Ser Asp Gly Ser Thr Thr Ala
     50                  55                  60

Asp Cys Leu Val Ser Asp Arg Lys Tyr Cys Gly Gly Ser Tyr Lys Gly
 65                  70                  75                  80

Ile Ile Asp Lys Leu Asp Tyr Ile Gln Gly Met Gly Phe Thr Ala Ile
                 85                  90                  95

Trp Ile Ser Pro Val Val Glu Gln Ile Pro Asp Asn Thr Ala Tyr Gly
             100                 105                 110

Tyr Ala Tyr His Gly Tyr Trp Met Lys Asn Ile Asp Glu Leu Asn Thr
         115                 120                 125

Asn Phe Gly Thr Ala Asp Glu Leu Lys Gln Leu Ala Ser Glu Leu His
    130                 135                 140

Ser Arg Ser Met Leu Leu Met Val Asp Val Val Tyr Asn His Tyr Ala
145                 150                 155                 160

Trp Asn Gly Asp Gly Ser Ser Val Asp Tyr Ser Ser Phe Thr Pro Phe
                165                 170                 175

Asn Gln Gln Ser Tyr Phe His Asp Tyr Cys Leu Ile Thr Asn Tyr Asn
            180                 185                 190

Asp Gln Thr Asn Val Glu Asp Cys Trp Glu Gly Asp Thr Glu Val Ser
        195                 200                 205

Leu Pro Asp Leu Ser Thr Glu Asp Asn Glu Val Ile Gly Val Phe Gln
    210                 215                 220

Thr Trp Val Ser Asp Phe Val Gln Asn Tyr Ser Ile Asp Gly Leu Arg
225                 230                 235                 240

Ile Asp Ser Ala Lys His Val Asp Thr Ala Ser Leu Thr Lys Phe Glu
                245                 250                 255

Asp Ala Ser Gly Val Tyr Asn Leu Gly Glu Val Tyr Gln Gly Asp Pro
            260                 265                 270

Thr Tyr Thr Cys Pro Tyr Gln Asn Tyr Met Lys Gly Val Thr Asn Tyr
        275                 280                 285

Pro Leu Tyr Tyr Pro Val Tyr Arg Phe Phe Ser Asp Thr Ser Ala Thr
    290                 295                 300

Ser Ser Glu Leu Thr Ser Met Ile Ser Thr Leu Gln Ser Ser Cys Ser
305                 310                 315                 320

Asp Val Ser Leu Leu Gly Asn Phe Ile Glu Asn His Asp Gln Val Arg
                325                 330                 335

Phe Pro Ser Val Thr Ser Asp Thr Ser Leu Ile Lys Asn Asp Met Ala
            340                 345                 350

Phe Ile Ile Leu Gly Asp Gly Ile Pro Ile Ile Tyr Tyr Gly Gln Glu
        355                 360                 365

Gln Gly Leu Asn Gly Gly Ser Asp Pro Ala Asn Arg Glu Ala Leu Trp
    370                 375                 380

Leu Ser Gly Tyr Asn Thr Asp Ser Glu Tyr Tyr Glu Leu Ile Ser Lys
385                 390                 395                 400

Leu Asn Gln Ile Arg Asn Gln Ala Ile Lys Lys Asp Ser Ala Tyr Ser
```

```
                405               410               415
Thr Tyr Lys Ser Ser Val Val Ser Ser Ser Asp His Tyr Ile Ala Thr
            420               425               430
Arg Lys Gly Ser Asp Ala Asn Gln Leu Ile Ser Ile Phe Asn Asn Leu
            435               440               445
Gly Ser Asn Gly Ser Gln Asp Ile Thr Val Ser Asn Thr Gly Tyr Ser
        450               455               460
Ser Gly Asp Lys Val Ile Asp Ile Ile Ser Cys Asn Ser Val Leu Ala
465               470               475               480
Gly Asp Ser Gly Ser Leu Ser Val Ser Ile Ser Gly Gly Met Pro Gln
                485               490               495
Val Tyr Ala Pro Ser Ser Val Leu Ser Gly Ser Gly Ile Cys Asn Gln
            500               505               510
```

<210> SEQ ID NO 3
<211> LENGTH: 2877
<212> TYPE: DNA
<213> ORGANISM: Schwanniomyces Occidentalis

<400> SEQUENCE: 3

| | | |
|---|---|---:|
| atgattttc tgaagctgat taaaagtata gtaattggtt tgggattagt tagtgctatc | | 60 |
| caagcagccc ctgcctcttc gattggatct agtgcttcag catctagttc aagtgagagt | | 120 |
| tctcaggcta caattcccaa tgatgtaaca ttaggtgtta aacaaattcc taatatcttt | | 180 |
| aatgactctg ctgtcgatgc taatgcagct gctaaagggt atgacttggt aaatgttact | | 240 |
| aatactccaa gaggattaac cggtatctta aaattaaaag aagctaccaa tatttatggt | | 300 |
| tatgattttg attatttaaa cttaactgtt gaataccaag ctgataccag attaaacgtt | | 360 |
| catattgaac caactgattt atctgatgta tttgttttac cagagcattt agttgttaaa | | 420 |
| ccactggtgg aaggtgatgc acaatcttat aacttcgaca attccgattt ggttttcgaa | | 480 |
| tactctaata ctgacttctc ctttgaagtt attagatcat ctactaaaga agttttattt | | 540 |
| tctactaaag gtaatccatt ggttttttca aatcaattca ttcaattcaa ttcgtcattg | | 600 |
| ccaaagaacc atgttattac tggtcttggt gaatctattc acggtttagt taacgaacca | | 660 |
| ggtagcgtta aaacattatt tgctaatgat gttggtgatc caatcgatgg taatatttat | | 720 |
| ggtgtccatc cagtttatct tgatcaaaga tatgacactg aaactaccca tgctgtttat | | 780 |
| tggagaactt ctgctattca agaagtatta atcggtgagg aatctattac ttggagagct | | 840 |
| ctttcaggtg ttattgattt atacttcttt agtggtccta caccaaaaga tgccattcaa | | 900 |
| cagtatgtca agagattgg tttaccagct ttccaaccat actggtcgtt aggttaccat | | 960 |
| caatgtagat ggggttacga tactatcgaa aaattatctg aagttgttga aaacttcaag | | 1020 |
| aaatttaata ttccattaga aactatctgg tcagacattg attacatgga ctcttataaa | | 1080 |
| gatttcactt atgatccaca cagattccca ctagatgaat atcgtaaatt ccttgatgag | | 1140 |
| ttgcacaaaa ataatcaaca ctatgttcct attttggatg ctgctattta cgttccaaac | | 1200 |
| ccaaacaatg ctacggataa cgaataccaa cctttccact atggtaatga aaccgatgtc | | 1260 |
| ttcttaaaga atccagatgg ttcattatat attggtgctg tttggcaggt tacactgttt | | 1320 |
| tccagatttc ttagcagaaa acattcagat atggataaag tcattaaaga ttggtatgaa | | 1380 |
| ttaactcctt tgatggtat ttgggctgat atgaatgaag tctcatcatt ctgtgttggt | | 1440 |
| tcttgtggta ctggtaaata cttcgaaaac ccagcatatc ctccatttac tgttggaagt | | 1500 |
| aaagctaccct cttatccagt tggtttcgat gtttctaacg catctgaatg gaatctatt | | 1560 |

-continued

```
caaagctcaa tttctgctac tgctaagact tcttcaactt cttccgtatc gtcgtcttca    1620
tccacaatcg attatatgaa cactttagct ccaggtaaag gtaatattaa ttatccacca    1680
tatgctattt acaacatgca aggtgactcc gatcttgcta ctcatgcagt atctccaaat    1740
gctacacatg ctgatggtac agttgaatat gatattcaca atctttatgg ttacttgcaa    1800
gaaaatgcta cttatcatgc attattggaa gttttcccta caagagacc attcatgatt     1860
tccagatcaa ccttccacg cgctggtaaa tggaccggcc attggggtgg tgacaacact     1920
gctgattggg cttatgctta cttctctatc cctcaagcat tctcaatggg tattgctggc    1980
cttccattct tggtgccga tgtttgtggt ttcaatggta attctgattc tgaattatgt     2040
tcaagatgga tgcaattagg ttctttcttc ccattctaca gaaaccacaa ctatttaggt    2100
gctattgatc aggaaccata tgtctgggaa tcagttgctg aagctactag aacttctatg    2160
gccattagat acttattatt accatattac tacactttat tacatgaatc tcatactact    2220
ggtttaccaa tcttaagagc tttctcgtgg caattcccta acgatcgttc cttaagtggt    2280
gtcgataacc aattttttgt cggtgatggt ttagttgtta ctcctgtctt agaacctggt    2340
gttgataagg ttaaaggtgt tttcccagga gctggtaaag aggaagttta ctacgactgg    2400
tacacccaaa gagaagttca cttttaaagac ggtaagaatg aaactttaga tgcaccatta   2460
ggtcatattc cattacacat tagaggtggt aacgtcttgc caactcaaga gccaggttat    2520
actgttgctg agtcaagaca aaatccattt ggtttaattg tcgctttaga taacgatggc    2580
aaagctcaag gtagcttata ccttgatgat ggtgaatcat tagtagtaga ctcttcattg    2640
ttggttagtt tctctgtttc tgataacaca ttatcagcat ctccatctgg tgactataaa    2700
gctgatcaac ctttagctaa tgttaccatc ttagggggttg gccataaacc aaaatcagtt   2760
aaatttgaaa acgctaatgt tgatttcacc tacaagaaat caaccgtttt cgttactggc    2820
ttagataaat acaccaagga tggtgcattt tctaaggatt tcaccattac ttggtaa       2877
```

<210> SEQ ID NO 4
<211> LENGTH: 969
<212> TYPE: PRT
<213> ORGANISM: Schwanniomyces Occidentalis

<400> SEQUENCE: 4

```
Cys Cys Ile Asp Glu Asn Thr Ala Leu Ile Ser Met Ile Phe Leu Lys
1               5                   10                  15

Leu Ile Lys Ser Ile Val Ile Gly Leu Gly Leu Val Ser Ala Ile Gln
            20                  25                  30

Ala Ala Pro Ala Ser Ser Ile Gly Ser Ser Ala Ser Ala Ser Ser Ser
        35                  40                  45

Ser Glu Ser Ser Gln Ala Thr Ile Pro Asn Asp Val Thr Leu Gly Val
    50                  55                  60

Lys Gln Ile Pro Asn Ile Phe Asn Asp Ser Ala Val Asp Ala Asn Ala
65                  70                  75                  80

Ala Ala Lys Gly Tyr Asp Leu Val Asn Val Thr Asn Thr Pro Arg Gly
                85                  90                  95

Leu Thr Gly Ile Leu Lys Leu Lys Glu Ala Thr Asn Ile Tyr Gly Tyr
            100                 105                 110

Asp Phe Asp Tyr Leu Asn Leu Thr Val Glu Tyr Gln Ala Asp Thr Arg
        115                 120                 125

Leu Asn Val His Ile Glu Pro Thr Asp Leu Ser Asp Val Phe Val Leu
    130                 135                 140
```

```
Pro Glu His Leu Val Val Lys Pro Leu Val Glu Gly Asp Ala Gln Ser
145                 150                 155                 160

Tyr Asn Phe Asp Asn Ser Asp Leu Val Phe Glu Tyr Ser Asn Thr Asp
                165                 170                 175

Phe Ser Phe Glu Val Ile Arg Ser Ser Thr Lys Glu Val Leu Phe Ser
            180                 185                 190

Thr Lys Gly Asn Pro Leu Val Phe Ser Asn Gln Phe Ile Gln Phe Asn
        195                 200                 205

Ser Ser Leu Pro Lys Asn His Val Ile Thr Gly Leu Gly Glu Ser Ile
210                 215                 220

His Gly Leu Val Asn Glu Pro Gly Ser Val Lys Thr Leu Phe Ala Asn
225                 230                 235                 240

Asp Val Gly Asp Pro Ile Asp Gly Asn Ile Tyr Gly Val His Pro Val
                245                 250                 255

Tyr Leu Asp Gln Arg Tyr Asp Thr Glu Thr Thr His Ala Val Tyr Trp
            260                 265                 270

Arg Thr Ser Ala Ile Gln Glu Val Leu Ile Gly Glu Ser Ile Thr
        275                 280                 285

Trp Arg Ala Leu Ser Gly Val Ile Asp Leu Tyr Phe Phe Ser Gly Pro
290                 295                 300

Thr Pro Lys Asp Ala Ile Gln Gln Tyr Val Lys Glu Ile Gly Leu Pro
305                 310                 315                 320

Ala Phe Gln Pro Tyr Trp Ser Leu Gly Tyr His Gln Cys Arg Trp Gly
                325                 330                 335

Tyr Asp Thr Ile Glu Lys Leu Ser Glu Val Val Glu Asn Phe Lys Lys
            340                 345                 350

Phe Asn Ile Pro Leu Glu Thr Ile Trp Ser Asp Ile Asp Tyr Met Asp
        355                 360                 365

Ser Tyr Lys Asp Phe Thr Tyr Asp Pro His Arg Phe Pro Leu Asp Glu
370                 375                 380

Tyr Arg Lys Phe Leu Asp Glu Leu His Lys Asn Asn Gln His Tyr Val
385                 390                 395                 400

Pro Ile Leu Asp Ala Ala Ile Tyr Val Pro Asn Pro Asn Asn Ala Thr
                405                 410                 415

Asp Asn Glu Tyr Gln Pro Phe His Tyr Gly Asn Glu Thr Asp Val Phe
            420                 425                 430

Leu Lys Asn Pro Asp Gly Ser Leu Tyr Ile Gly Ala Val Trp Gln Val
        435                 440                 445

Thr Leu Phe Ser Arg Phe Leu Ser Arg Lys His Ser Asp Met Asp Lys
450                 455                 460

Val Ile Lys Asp Trp Tyr Glu Leu Thr Pro Phe Asp Gly Ile Trp Ala
465                 470                 475                 480

Asp Met Asn Glu Val Ser Ser Phe Cys Val Gly Ser Cys Gly Thr Gly
                485                 490                 495

Lys Tyr Phe Glu Asn Pro Ala Tyr Pro Pro Phe Thr Val Gly Ser Lys
            500                 505                 510

Ala Thr Ser Tyr Pro Val Gly Phe Asp Val Ser Asn Ala Ser Glu Trp
        515                 520                 525

Lys Ser Ile Gln Ser Ser Ile Ser Ala Thr Ala Lys Thr Ser Ser Thr
530                 535                 540

Ser Ser Val Ser Ser Ser Ser Thr Ile Asp Tyr Met Asn Thr Leu
545                 550                 555                 560
```

```
Ala Pro Gly Lys Gly Asn Ile Asn Tyr Pro Pro Tyr Ala Ile Tyr Asn
            565                 570                 575

Met Gln Gly Asp Ser Asp Leu Ala Thr His Ala Val Ser Pro Asn Ala
            580                 585                 590

Thr His Ala Asp Gly Thr Val Glu Tyr Asp Ile His Asn Leu Tyr Gly
            595                 600                 605

Tyr Leu Gln Glu Asn Ala Thr Tyr His Ala Leu Leu Glu Val Phe Pro
    610                 615                 620

Asn Lys Arg Pro Phe Met Ile Ser Arg Ser Thr Phe Pro Arg Ala Gly
625                 630                 635                 640

Lys Trp Thr Gly His Trp Gly Asp Asn Thr Ala Asp Trp Ala Tyr
                645                 650                 655

Ala Tyr Phe Ser Ile Pro Gln Ala Phe Ser Met Gly Ile Ala Gly Leu
            660                 665                 670

Pro Phe Phe Gly Ala Asp Val Cys Gly Phe Asn Gly Asn Ser Asp Ser
            675                 680                 685

Glu Leu Cys Ser Arg Trp Met Gln Leu Gly Ser Phe Phe Pro Phe Tyr
            690                 695                 700

Arg Asn His Asn Tyr Leu Gly Ala Ile Asp Gln Glu Pro Tyr Val Trp
705                 710                 715                 720

Glu Ser Val Ala Glu Ala Thr Arg Thr Ser Met Ala Ile Arg Tyr Leu
                725                 730                 735

Leu Leu Pro Tyr Tyr Thr Leu Leu His Glu Ser His Thr Thr Gly
                740                 745                 750

Leu Pro Ile Leu Arg Ala Phe Ser Trp Gln Phe Pro Asn Asp Arg Ser
            755                 760                 765

Leu Ser Gly Val Asp Asn Gln Phe Phe Val Gly Asp Gly Leu Val Val
    770                 775                 780

Thr Pro Val Leu Glu Pro Gly Val Asp Lys Val Lys Gly Val Phe Pro
785                 790                 795                 800

Gly Ala Gly Lys Glu Glu Val Tyr Tyr Asp Trp Tyr Thr Gln Arg Glu
                805                 810                 815

Val His Phe Lys Asp Gly Lys Asn Glu Thr Leu Asp Ala Pro Leu Gly
                820                 825                 830

His Ile Pro Leu His Ile Arg Gly Gly Asn Val Leu Pro Thr Gln Glu
            835                 840                 845

Pro Gly Tyr Thr Val Ala Glu Ser Arg Gln Asn Pro Phe Gly Leu Ile
            850                 855                 860

Val Ala Leu Asp Asn Asp Gly Lys Ala Gln Gly Ser Leu Tyr Leu Asp
865                 870                 875                 880

Asp Gly Glu Ser Leu Val Val Asp Ser Ser Leu Leu Val Ser Phe Ser
            885                 890                 895

Val Ser Asp Asn Thr Leu Ser Ala Ser Pro Ser Gly Asp Tyr Lys Ala
            900                 905                 910

Asp Gln Pro Leu Ala Asn Val Thr Ile Leu Gly Val Gly His Lys Pro
            915                 920                 925

Lys Ser Val Lys Phe Glu Asn Ala Asn Val Asp Phe Thr Tyr Lys Lys
            930                 935                 940

Ser Thr Val Phe Val Thr Gly Leu Asp Lys Tyr Thr Lys Asp Gly Ala
945                 950                 955                 960

Phe Ser Lys Asp Phe Thr Ile Thr Trp
                965
```

```
<210> SEQ ID NO 5
<211> LENGTH: 2415
<212> TYPE: DNA
<213> ORGANISM: APRIGILIS NIGER

<400> SEQUENCE: 5
atggcgcact caatgtctcg tcccgtggct gccactgccg ctgctctgtt ggctctggct      60
cttccccaag ctcttgccca ggccaacacc agctatgtcg attacaacgt cgaggccaac     120
cctgacttgt acccttttgtg catagaaacc atcccactga gcttccccga ctgccagaat    180 ggcccccctgc gcagccacct catctgcgac gaatcagcca cccctatga ccgagcagca    240 tcgctcatct cgctcttcac gctggacgag ctgatcgcca acaccggcaa caccggcctc    300
ggtgtctccc gactgggcct ccctgcatac aagtatgga gtgaagcact tcacggcctc    360
gaccgtgcca acttcagcga ctcaggctcc tacaattggg ctacttcatt cccccaacct   420
atcttgacca ccgcggccct caaccgcacc ctcattcacc aaatcgcctc catcatctcc   480
acccaaggcc gtgccttcaa caacgccggc cgctacggcc tcgatgtcta cgccccaac    540 atcaacacct tccgccaccc cgtctggggt cgcggacaag aaactccagg agaggacgtc   600
tctctcgccg ccgtctacgc ctacgaatac atcaccggca tccagggtcc cgacccagac  660
tcaaacctca acttgccgc cacggccaag cactacgccg gctatgacat cgagaactgg    720
cacaaccact cccgcctggg caatgatatg aacatcaccc agcaagacct gtcagaatac   780
tacactcccc agttccacgt cgccgcccgc gacgccaaag tccacagtgt catgtgtgcc   840
tataacgccg tcgacggcgt ccctgcctgc gccgactctt acttcctcca gaccctcctc   900
cgcgacacct tcggattcgt tgaccacggc tacgtctcca gcgactgcga cgccgcctac   960
aacatctaca tcccccacgg ctacgcctcc tcccaggctg ccgctgccgc tgaggccatc  1020
ctcgctggca ctgacatcga ctgcggtacc acctaccaat ggcacctgaa cgagtccatc 1080
actgcgggag atctctctcg cgatgatatc gagaagggtg tgatccgcct ctacacgacc 1140
cttgtgcagg ccggatactt cgactccaat accaccaagg cgaacaaccc ctaccgcgac 1200
ctcacctggt ccgatgtcct cgagacggac gcatggaaca tctcctacca gccgcgacg  1260 cagggcattg tccttctcaa gaactccaac aacgtccttc ccctcaccga aaagcttac  1320 ccaccatcca acaccaccgt cgcccttatc ggtccctggg ccaacgccac cacccaactc 1380
ctgggcaact actacggcaa cgctcccctac atgatcagcc ccgcgccgc gttcgaagaa 1440 gccggataca aagtcaactt cgccgaaggc accggtatct cctccacaag cacctcgggc 1500
ttcgcagccg ccttatccgc cgcccggtcc gccgacgtga tcatctacgc cggtggtatc 1560
gacaatactc ttgaagcgga ggcactggat cgcgagagca tcgcatggcc gggtaaccaa 1620
ctggacttga tccaaaagct cgcctcgtcg gccggaagca agccgctcat cgttctccaa 1680
atgggcggcg gacaggtcga ttcctcgtcc ctcaagaaca cacgaacgt cactgcactc  1740 ctctggggcg ataccccgg ccaatccggc ggtttcgctc tgagagacat catcacggga 1800
aagaagaacc ccgcgggtag actagtcacg acacaatacc cagccagcta cgcggaggag 1860
ttccccgcga cggatatgaa cctccgtcct gagggtgata ccccggcca acatacaaa  1920 tggtacaccg gcgaagcagt gtacgagttc ggccacggat tatctacac gaccttcgcg 1980 gaatcatcca gcaacaccac tacgaaggaa gttaagctca acatccagga cattctttcc  2040
cagacacacg aagagctagc ctcaattacg cagctccctg tgctgaactt cactgccaat 2100
atcaagaaca ctggaaaagct ggaatcggat tacaccgcta tggtattcgc caataccctct 2160
```

```
gatgccggtc cggcgccgta cccggtgaag tggctggtcg ggtgggatcg gcttggggat    2220
gtgaaggtcg gggagacgag ggagttgagg gttcccgttg aggtgggggag ctttgcgagg    2280 gtgaatgagg atggcgattg ggtgttgttt ccgggaacgt ttgagttggc gttgaacctg    2340
gagaggaagg ttagggtgaa ggttgttctt gagggtgagg aggaagtcgt gctgaagtgg    2400
cctgggaagg agtag                                                     2415
```

<210> SEQ ID NO 6
<211> LENGTH: 804
<212> TYPE: PRT
<213> ORGANISM: APRIGILIS NIGER

<400> SEQUENCE: 6

```
Met Ala His Ser Met Ser Arg Pro Val Ala Thr Ala Ala Ala Leu
1               5                   10                  15

Leu Ala Leu Ala Leu Pro Gln Ala Leu Ala Gln Ala Asn Thr Ser Tyr
                20                  25                  30

Val Asp Tyr Asn Val Glu Ala Asn Pro Asp Leu Tyr Pro Leu Cys Ile
            35                  40                  45

Glu Thr Ile Pro Leu Ser Phe Pro Asp Cys Gln Asn Gly Pro Leu Arg
    50                  55                  60

Ser His Leu Ile Cys Asp Glu Ser Ala Thr Pro Tyr Asp Arg Ala Ala
65                  70                  75                  80

Ser Leu Ile Ser Leu Phe Thr Leu Asp Glu Leu Ile Ala Asn Thr Gly
                85                  90                  95

Asn Thr Gly Leu Gly Val Ser Arg Leu Gly Leu Pro Ala Tyr Gln Val
            100                 105                 110

Trp Ser Glu Ala Leu His Gly Leu Asp Arg Ala Asn Phe Ser Asp Ser
        115                 120                 125

Gly Ser Tyr Asn Trp Ala Thr Ser Phe Pro Gln Pro Ile Leu Thr Thr
    130                 135                 140

Ala Ala Leu Asn Arg Thr Leu Ile His Gln Ile Ala Ser Ile Ile Ser
145                 150                 155                 160

Thr Gln Gly Arg Ala Phe Asn Asn Ala Gly Arg Tyr Gly Leu Asp Val
                165                 170                 175

Tyr Ala Pro Asn Ile Asn Thr Phe Arg His Pro Val Trp Gly Arg Gly
            180                 185                 190

Gln Glu Thr Pro Gly Glu Asp Val Ser Leu Ala Ala Val Tyr Ala Tyr
        195                 200                 205

Glu Tyr Ile Thr Gly Ile Gln Gly Pro Asp Pro Asp Ser Asn Leu Lys
    210                 215                 220

Leu Ala Ala Thr Ala Lys His Tyr Ala Gly Tyr Asp Ile Glu Asn Trp
225                 230                 235                 240

His Asn His Ser Arg Leu Gly Asn Asp Met Asn Ile Thr Gln Gln Asp
                245                 250                 255

Leu Ser Glu Tyr Tyr Thr Pro Gln Phe His Val Ala Ala Arg Asp Ala
            260                 265                 270

Lys Val His Ser Val Met Cys Ala Tyr Asn Ala Val Asp Gly Val Pro
        275                 280                 285

Ala Cys Ala Asp Ser Tyr Phe Leu Gln Thr Leu Leu Arg Asp Thr Phe
    290                 295                 300

Gly Phe Val Asp His Gly Tyr Val Ser Ser Asp Cys Asp Ala Ala Tyr
305                 310                 315                 320

Asn Ile Tyr Asn Pro His Gly Tyr Ala Ser Ser Gln Ala Ala Ala Ala
```

```
                      325                 330                 335
Ala Glu Ala Ile Leu Ala Gly Thr Asp Ile Asp Cys Gly Thr Thr Tyr
                340                 345                 350
Gln Trp His Leu Asn Glu Ser Ile Thr Ala Gly Asp Leu Ser Arg Asp
                355                 360                 365
Asp Ile Glu Lys Gly Val Ile Arg Leu Tyr Thr Thr Leu Val Gln Ala
370                 375                 380
Gly Tyr Phe Asp Ser Asn Thr Thr Lys Ala Asn Asn Pro Tyr Arg Asp
385                 390                 395                 400
Leu Thr Trp Ser Asp Val Leu Glu Thr Asp Ala Trp Asn Ile Ser Tyr
                405                 410                 415
Gln Ala Ala Thr Gln Gly Ile Val Leu Leu Lys Asn Ser Asn Asn Val
                420                 425                 430
Leu Pro Leu Thr Glu Lys Ala Tyr Pro Pro Ser Asn Thr Thr Val Ala
                435                 440                 445
Leu Ile Gly Pro Trp Ala Asn Ala Thr Thr Gln Leu Leu Gly Asn Tyr
                450                 455                 460
Tyr Gly Asn Ala Pro Tyr Met Ile Ser Pro Arg Ala Ala Phe Glu Glu
465                 470                 475                 480
Ala Gly Tyr Lys Val Asn Phe Ala Glu Gly Thr Gly Ile Ser Ser Thr
                485                 490                 495
Ser Thr Ser Gly Phe Ala Ala Ala Leu Ser Ala Ala Arg Ser Ala Asp
                500                 505                 510
Val Ile Ile Tyr Ala Gly Gly Ile Asp Asn Thr Leu Glu Ala Glu Ala
                515                 520                 525
Leu Asp Arg Glu Ser Ile Ala Trp Pro Gly Asn Gln Leu Asp Leu Ile
                530                 535                 540
Gln Lys Leu Ala Ser Ser Ala Gly Ser Lys Pro Leu Ile Val Leu Gln
545                 550                 555                 560
Met Gly Gly Gly Gln Val Asp Ser Ser Ser Leu Lys Asn Asn Thr Asn
                565                 570                 575
Val Thr Ala Leu Leu Trp Gly Gly Tyr Pro Gly Gln Ser Gly Gly Phe
                580                 585                 590
Ala Leu Arg Asp Ile Ile Thr Gly Lys Lys Asn Pro Ala Gly Arg Leu
                595                 600                 605
Val Thr Thr Gln Tyr Pro Ala Ser Tyr Ala Glu Glu Phe Pro Ala Thr
                610                 615                 620
Asp Met Asn Leu Arg Pro Glu Gly Asp Asn Pro Gly Gln Thr Tyr Lys
625                 630                 635                 640
Trp Tyr Thr Gly Glu Ala Val Tyr Glu Phe Gly His Gly Leu Phe Tyr
                645                 650                 655
Thr Thr Phe Ala Glu Ser Ser Asn Thr Thr Thr Lys Glu Val Lys
                660                 665                 670
Leu Asn Ile Gln Asp Ile Leu Ser Gln Thr His Glu Glu Leu Ala Ser
                675                 680                 685
Ile Thr Gln Leu Pro Val Leu Asn Phe Thr Ala Asn Ile Lys Asn Thr
                690                 695                 700
Gly Lys Leu Glu Ser Asp Tyr Thr Ala Met Val Phe Ala Asn Thr Ser
705                 710                 715                 720
Asp Ala Gly Pro Ala Pro Tyr Pro Val Lys Trp Leu Val Gly Trp Asp
                725                 730                 735
Arg Leu Gly Asp Val Lys Val Gly Glu Thr Arg Glu Leu Arg Val Pro
                740                 745                 750
```

Val Glu Val Gly Ser Phe Ala Arg Val Asn Glu Asp Gly Asp Trp Val
        755                 760                 765

Leu Phe Pro Gly Thr Phe Glu Leu Ala Leu Asn Leu Glu Arg Lys Val
    770                 775                 780

Arg Val Lys Val Val Leu Glu Gly Glu Glu Val Val Leu Lys Trp
785                 790                 795                 800

Pro Gly Lys Glu

<210> SEQ ID NO 7
<211> LENGTH: 690
<212> TYPE: DNA
<213> ORGANISM: TRICHODERMA REESEI

<400> SEQUENCE: 7
atggttgcct tttccagcct catctgcgct ctcaccagca tcgccagtac tctggcgatg    60
cccacaggcc tcgagcctga gagcagtgtc aacgtcacag agcgtggcat gtacgacttt   120
gttcttggag ctcacaatga tcatcgccgt cgtgctagca tcaactacga ccaaaactac   180
caaactggcg gacaagtcag ctattcgcct tccaacactg gcttctcagt gaactggaac   240
actcaagatg actttgttgt gggcgttggt tggacgactg gatcttctgc tcccatcaac   300
tttggcggct cttttagtgt caacagcgga actggcctgc tttccgtcta tggctggagc   360
accaacccac tggttgagta ctacatcatg gaggacaacc acaactaccc agcacagggt   420
accgtcaagg gaaccgtcac cagcgacgga gccacttaca ccatctggga ataccccgt   480 gtcaacgagc cttccatcca gggcacagcg accttcaacc agtacatttc cgtgcggaac   540
tcgcccagga ccagcggaac tgttactgtg cagaaccact caatgcttg gcctcgctt   600 ggcctgcacc ttgggcagat gaactaccag gttgtcgctg tcgaaggctg gggtggtagt   660
ggttctgcct cacagagtgt cagcaactag                                    690

<210> SEQ ID NO 8
<211> LENGTH: 229
<212> TYPE: PRT
<213> ORGANISM: TRICHODERMA REESEI

<400> SEQUENCE: 8

Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
        35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser
                85                  90                  95

Ala Pro Ile Asn Phe Gly Gly Ser Phe Ser Val Asn Ser Gly Thr Gly
            100                 105                 110

Leu Leu Ser Val Tyr Gly Trp Ser Thr Asn Pro Leu Val Glu Tyr Tyr
        115                 120                 125

Ile Met Glu Asp Asn His Asn Tyr Pro Ala Gln Gly Thr Val Lys Gly
    130                 135                 140

```
Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
                180                 185                 190

His Phe Asn Ala Trp Ala Ser Leu Gly Leu His Leu Gly Gln Met Asn
            195                 200                 205

Tyr Gln Val Val Ala Val Glu Gly Trp Gly Gly Ser Gly Ser Ala Ser
210                 215                 220

Gln Ser Val Ser Asn
225

<210> SEQ ID NO 9
<211> LENGTH: 380
<212> TYPE: DNA
<213> ORGANISM: APRIGILIS NIGER

<400> SEQUENCE: 9
aaaatactat tctgttgatg gctctagggg atgagagtca gcctattact ggatatgcat      60
agtggtgata cgatgtatat agctctatga agtaattagt tcaagtggga ataccccttt    120
cacacatata gtatgctgtt attccgaaat agggatcatt tctgattaat agtagcggta    180
gcgatggtca cacgacttaatgttcccc attgtaccgg aagtaacaat tccagtgacc       240
```

```
gcgatggtca cacgacttaa tgttcccc attgtaccgg aagtaacaat tccagtgacc      240
tcttagaaga agacagcaa gaaaagtaa gaaagggaaa ttgatcaaaa ataaggcca       300 tctacagcct attcacattt agccggatct gcaatacagc tacagaaata agtttgtta    360 ggctgcttgc tagcatagct                                                 380

<210> SEQ ID NO 10
<211> LENGTH: 412
<212> TYPE: DNA
<213> ORGANISM: TRICHODERMA REESEI

<400> SEQUENCE: 10
agcttggaga cgtggaagga catccgcctt tgagaagcg tgtttgaaaa tagttctttt      60
tctggtttat atcgtttatg aagtgatgag atgaaaagct gaaatagcga gtataggaaa   120
atttaatgaa aattaaatta aatattttct taggctatta gtcaccttca aaatgccggc    180
cgcttctaag aacgttgtca tgatcgacaa ctacgactcg tttacctgga acctgtacga   240
gtacctgtgt caggagggag ccaatgtcga ggttttcagg aacgatcaga tcaccattcc   300
ggagattgag cagctcaagc cggacgttgt ggtgatatcc cctggtcctg gccatccaag   360
aacagactcg ggaatatctc gcgacgtgat cagccatttt aaaggcaaga tt           412

<210> SEQ ID NO 11
<211> LENGTH: 621
<212> TYPE: DNA
<213> ORGANISM: HANSENELLA POLYMORPHA

<400> SEQUENCE: 11
aattatcatt aataatcact catgatccct gcgtctagag gttggtctag accacatccg    60
tgcaccagac aagacacggc ccacggaggt aaaggtgcca actcgcaaag tgcaacaacc   120
atggctctcc agcacggtgc gtggggtaaa gacaatctcc gggaaccgat cccgaaaccg   180
agaaagaggg ttttaagcgt gtgtcctttg cggaggcggt gtagcacttc ttattgtcct   240
ttgggccgct ccggcggttg agcttccaca gaacatcctt gcacggacaa gcagtcccgg   300
```

```
agacgccatg ttgggtgata cccacttctg gctgtacaga gctttatatc accttacctg      360
gcgctagagt agcccaatt cccgactcac accaccctca catgcagaac taaccaataa      420
ggtaattaat taacacgata tagctcgtgg tgaacactgg cccggagtag tcatacgtgt      480
aggtttttgg cgtgatgaaa atcaggtgga gcacgacttt tcgtaatgtt cgggagggag      540
tgctgcaaac ggtatataag gaccagtttt tctcgcaaca ttatcaattg ctctttagta      600
caaagataat atagaaacaa a                                                621

<210> SEQ ID NO 12
<211> LENGTH: 412
<212> TYPE: DNA
<213> ORGANISM: HANSENELLA POLYMORPHA

<400> SEQUENCE: 12
agcttggaga cgtggaagga cataccgctt ttgagaagcg tgtttgaaaa tagttctttt       60
tctggtttat atcgtttatg aagtgatgag atgaaaagct gaaatagcga gtataggaaa      120
atttaatgaa aattaaatta aatatttct taggctatta gtcaccttca aaatgccggc       180
cgcttctaag aacgttgtca tgatcgacaa ctacgactcg tttacctgga acctgtacga      240
gtacctgtgt caggagggag ccaatgtcga ggttttcagg aacgatcaga tcaccattcc      300
ggagattgag cagctcaagc cggacgttgt ggtgatatcc cctggtcctg gccatccaag      360
aacagactcg ggaatatctc gcgacgtgat cagccatttt aaaggcaaga tt             412
```